(12) United States Patent
Konstantino et al.

(10) Patent No.: US 12,369,933 B2
(45) Date of Patent: Jul. 29, 2025

(54) ASPIRATION CATHETER

(71) Applicant: Expanse Technology Partners, LLC, Pleasanton, CA (US)

(72) Inventors: Eitan Konstantino, Orinda, CA (US); Matthew Drummond Ritch, Pleasanton, CA (US); Stephanie Morgan Boula, Fremont, CA (US); Tanhum Feld, Moshav Merhavya (IL)

(73) Assignee: Expanse Technology Partners, LLC, Pleasanton, CA (US)

( * ) Notice: Subject to any disclaimer, the term of this patent is extended or adjusted under 35 U.S.C. 154(b) by 0 days.

(21) Appl. No.: 18/590,717

(22) Filed: Feb. 28, 2024

(65) Prior Publication Data

US 2024/0197342 A1  Jun. 20, 2024

Related U.S. Application Data

(63) Continuation of application No. 17/658,244, filed on Apr. 6, 2022, now Pat. No. 11,944,330.

(Continued)

(51) Int. Cl.
*A61B 17/00* (2006.01)
*A61B 17/22* (2006.01)
(Continued)

(52) U.S. Cl.
CPC .... *A61B 17/22* (2013.01); *A61B 2017/00292* (2013.01); *A61B 2017/22079* (2013.01);
(Continued)

(58) Field of Classification Search
CPC .............. A61B 17/22; A61B 17/22031; A61B 17/3205; A61B 17/32075; A61B 18/00;
(Continued)

(56) References Cited

U.S. PATENT DOCUMENTS

| 217,711 A | 7/1879 | Shiland |
|---|---|---|
| 1,595,180 A | 8/1926 | Fisher |

(Continued)

FOREIGN PATENT DOCUMENTS

| EP | 2362751 | 9/2016 |
|---|---|---|
| WO | WO 2014/151209 | 9/2014 |

(Continued)

OTHER PUBLICATIONS

International Search Report and Written Opinion of PCT/US2022/023743, Dated Jun. 14, 2022 in 32 pages.

(Continued)

*Primary Examiner* — Catharine L Anderson
*Assistant Examiner* — Jihad Dakkak
(74) *Attorney, Agent, or Firm* — Knobbe Martens Olson & Bear LLP

(57) ABSTRACT

Systems and methods for performing aspiration thrombectomy. The aspiration catheter assembly can include a support catheter and an aspiration catheter extending through the support catheter. The catheter assembly can include a distal valve apparatus that can control a level of vacuum at a distal end of the catheter system. Irrigation can flow between the support catheter and the aspiration catheter to flush the catheter assembly.

14 Claims, 15 Drawing Sheets

Related U.S. Application Data

(60) Provisional application No. 63/267,031, filed on Jan. 21, 2022, provisional application No. 63/200,995, filed on Apr. 7, 2021.

(51) Int. Cl.
*A61M 25/06* (2006.01)
*A61M 39/24* (2006.01)

(52) U.S. Cl.
CPC ............... *A61B 2217/007* (2013.01); *A61M 2025/0681* (2013.01); *A61M 2039/2433* (2013.01)

(58) Field of Classification Search
CPC ........... A61B 2017/00292; A61B 2017/22034; A61B 2017/22035; A61B 2017/22079; A61B 2017/22084; A61B 2017/320716; A61B 2018/00464; A61B 2217/005; A61B 2217/007; A61M 1/00; A61M 1/84; A61M 2025/0004; A61M 2025/0076; A61M 2025/0681; A61M 2039/0646; A61M 2039/2433; A61M 2205/3334; A61M 2205/3344; A61M 2206/20; A61M 2210/0693; A61M 25/0074; A61M 25/0075

See application file for complete search history.

(56) References Cited

U.S. PATENT DOCUMENTS

| | | | |
|---|---|---|---|
| 4,023,559 A | 5/1977 | Gaskell | |
| 5,261,416 A | 11/1993 | Taussig | |
| 5,827,229 A | 10/1998 | Auth et al. | |
| 9,289,562 B2 | 3/2016 | Thorne et al. | |
| 9,510,854 B2 | 12/2016 | Mallaby | |
| 9,681,882 B2 | 6/2017 | Garrison et al. | |
| 10,188,409 B2 | 1/2019 | Smalling | |
| 10,192,230 B2 | 1/2019 | Look et al. | |
| 10,226,263 B2 | 3/2019 | Look et al. | |
| 10,335,260 B2 | 7/2019 | Janardhan et al. | |
| 10,456,555 B2 | 10/2019 | Garrison et al. | |
| 10,499,944 B2 | 12/2019 | Mallaby | |
| 10,531,883 B1 | 1/2020 | Deville et al. | |
| 10,661,053 B2 | 5/2020 | Yang et al. | |
| 10,716,915 B2 | 7/2020 | Ogle et al. | |
| 10,722,253 B2 | 7/2020 | Deville et al. | |
| 10,835,711 B2 | 11/2020 | Yang et al. | |
| 11,096,712 B2 | 8/2021 | Teigen et al. | |
| 11,197,683 B1 | 12/2021 | Teigen et al. | |
| 11,452,841 B2 | 9/2022 | Jalgaonkar et al. | |
| 11,607,523 B2 | 3/2023 | Chou | |
| 11,633,571 B2 | 4/2023 | Garrison et al. | |
| 11,678,905 B2 | 6/2023 | Look et al. | |
| 11,701,490 B2 | 7/2023 | San | |
| 11,944,330 B2 | 4/2024 | Konstantino et al. | |
| 2002/0111585 A1* | 8/2002 | Lafontaine | A61M 39/0606 604/93.01 |
| 2002/0193742 A1 | 12/2002 | Davey | |
| 2012/0271231 A1 | 10/2012 | Agrawal | |
| 2014/0102445 A1* | 4/2014 | Clement | A61M 1/77 128/202.13 |
| 2016/0206340 A1* | 7/2016 | Vetter | A61B 17/3201 |
| 2017/0027752 A1 | 2/2017 | McCary et al. | |
| 2017/0265879 A1* | 9/2017 | Washburn | A61B 17/3496 |
| 2017/0274180 A1* | 9/2017 | Garrison | A61M 25/01 |
| 2017/0319776 A1* | 11/2017 | Eisner | A61M 39/22 |
| 2018/0042623 A1 | 2/2018 | Batiste | |
| 2018/0338770 A1 | 11/2018 | Mogi et al. | |
| 2019/0239910 A1 | 8/2019 | Brady et al. | |
| 2019/0336727 A1* | 11/2019 | Yang | A61B 17/22 |
| 2020/0129231 A1 | 4/2020 | McCaffrey et al. | |
| 2020/0129316 A1 | 4/2020 | Kawwas et al. | |
| 2020/0129742 A1 | 4/2020 | Cope et al. | |
| 2020/0205845 A1 | 7/2020 | Yang et al. | |
| 2020/0289136 A1 | 9/2020 | Chou | |
| 2020/0367917 A1 | 11/2020 | Teigen et al. | |
| 2022/0323087 A1 | 10/2022 | Konstantino et al. | |
| 2022/0378449 A1 | 12/2022 | Look et al. | |
| 2022/0387052 A1 | 12/2022 | Look et al. | |
| 2023/0263995 A1 | 8/2023 | Chou et al. | |
| 2023/0277806 A1 | 9/2023 | Chou et al. | |
| 2023/0310803 A1 | 10/2023 | San | |
| 2024/0197342 A1 | 6/2024 | Konstantino et al. | |

FOREIGN PATENT DOCUMENTS

| | | |
|---|---|---|
| WO | WO 2017/062927 | 4/2017 |
| WO | WO 2018/019829 | 2/2018 |
| WO | WO 2019/152898 | 8/2019 |
| WO | WO 2022/020366 | 2/2022 |
| WO | WO 2022/216882 | 10/2022 |
| WO | WO 2023/196248 | 10/2023 |

OTHER PUBLICATIONS

Bloomfield "How Everything Works: Making Physics Out of the Ordinary", 2007, John Wiley & Sons.

Chitsaz et al., "Three-Dimensional Numerical Simulations of Aspiration Process: Evaluation of Two Penumbra Aspiration Catheters Performance", 2018, 42(12), E406-E409, Artificial Organs.

Elder et al., "The Search for the Holy Grail of New PE Devices" 2020, 19(7), 13-17, Supplement to Endovascular Today.

Froehler et al., "Comparison of Vacuum Pressures and Forces Generated by Different Cathetersand Pumps for Aspiration Thrombectomy in Acute Ischemic Stroke", 2017, 6(3-4), 199-206, Interventional Neurology.

Good et al., "Development of a Computational Model for Acute Ischemic Stroke Recanalization through Cyclic Aspiration", 2020, 19(2), 761-778, Biomechanics and Modeling in Mechanobiology.

Jansen et al., "Neurothrombectomy for the Treatment of Acute Ischemic Stroke: Results from the TREVO Study", 2013, 36(3), 218-225, Cerebrovascular Diseases.

Johnson et al., Review of Mechanical Testing and Modelling of Thrombus Material for Vascular Implant and Device Design_, 2017, 45(11), 2494-2508, Annals of Biomedical Engineering.

"K122756", Accessed Jan. 25, 2021, https://www.accessdata.fda.gov/cdrh_docs/pdf12/K122756.pdf., 2012, in 6 pages.

"K172448", Accessed Jan. 25, 2021, https://www.accessdata.fda.gov/cdrh_docs/pdf17/K172448.pdf., 2017, in 17 pages.

Kalenik "Empirical Formulas for Calculation of Negative Pressure Difference in Vacuum Pipelines", 2015, 7(10), 5284-5304, Water.

Klopfenstein et al., "Middle Cerebral Artery Stenosis: Endovascular and Surgical Options", 2005, 15(3), 175-189, Skull Base.

Li, "Fluid Flow Analysis of a Single-Stage Centrifugal Fan with a Ported Diffuser", 2009, 3(2), 147-163, Engineering Applications of Computational Fluid Mechanics.

Madjidyar et al., "Influence of Thrombus Composition on Thrombectomy: ADAPT vs. Balloon Guide Catheter and Stent Retriever in a Flow Model", 2020, 192(3), 257-263, RöFo— Fortschritte Auf Dem Gebiet Der Röntgenstrahlen Und Der Bildgebenden Verfahren.

Mathewson, "Vacuum System Design", in 15 pages.

"Overview of Hydraulic Transients", Concept. Accessed Dec. 23, 2020. https://docs.bentley.com/LiveContent/web/Bentley%20HAMMER%20SS6-v1/en/GUID-0626B27E-81E7-4F52-9A9B-B1E2B8ADCEC0.html., in 1 page.

Pai et al., "Microsurgical Anatomy of the Middle Cerebral Artery", 2005, 53(2), 186-190, Neurology India.

Park et al., "Analytical Model of Fluid Flow through Closed Structures for Vacuum Tube Systems", 2015, Hindawi Publishing Corporation, in 7 pages.

Pennati et al., "Numerical Simulation of Thrombus Aspiration in Two Realistic Models of Catheter Tips" 2010, 34(4), 301-310, Artificial Organs.

(56) References Cited

OTHER PUBLICATIONS

Rai et al., "Cerebrovascular Geometry in the Anterior Circulation: An Analysis of Diameter, Length and the Vessel Taper", 2013, 5(4), 371-375, Journal of NeuroInterventional Surgery.
Reci et al., "Variations of Shape, Length, Branching, and End Trunks of M1 Segment of Middle Cerebral Artery", 2019, 5(1), 052-056, Journal of Neurology, Neurological Science and Disorders.
"Revealing the Magic in Everyday Life (PHYS0607)", Accessed Jan. 12, 2021, https://www.physics.hku.hk/~phys0607/lectures/chap03.html., in 11 pages.
Shi et al., "Suction Force-Suction Distance Relation during Aspiration Thrombectomy for Ischemic Stroke: A Computational Fluid Dynamics Study", 2017, 3, 1-8, Physics in Medicine.
Simon et al., "Exploring the Efficacy of Cyclic vs Static Aspiration in a Cerebral Thrombectomy Model: An Initial Proof of Concept Study", 2014, 6(9), 677-683, Journal of NeuroInterventional Surgery.
Simon et al., "Hydrodynamic Comparison of the Penumbra System and Commonly Available Syringes in Forced-Suction Thrombectomy", 2014, 6(3), 205-211, Journal of Neurointerventional Surgery.
Sukel, "Vacuum Wars", 2018, 140(10), 42-47, Mechanical Engineering.
Umansky et al., "Microsurgical Anatomy of the Proximal Segments of the Middle Cerebral Artery", 1984, 61(3), 458-467, Journal of Neurosurgery.
"Vacuum—Evacuation Time", Accessed Jan. 12, 2021, https://www.engineeringtoolbox.com/vacuum-evacuation-time-d_844.html., in 8 pages.
"Vacuum Technology.Pdf.", Accessed Jan. 12, 2021, http://newton.phys.uaic.ro/data/pdf/Vacuum%20Technology.pdf., Fundamentals of Vacuum Technology, in 200 pages.
Vargas et al., "Efficacy of Beveled Tip Aspiration Catheter in Mechanical Thrombectomy for Acute Ischemic Stroke", 2020, 1-5, Journal of NeuroInterventional Surgery.
Wei et al., "The Use and Utility of Aspiration Thrombectomy in Acute Ischemic Stroke: A Systematic Review and Meta-Analysis", 2017, 38(10), 1978-1983, AJNR. American Journal of Neuroradiology.
Welch et al., "The Pressure Profile in a Long Outgassing Vacuum Tube", 1973, 23(8), 271-276, Vacuum.
Yaeger et al., "A Technical Comparison of Thrombectomy Vacuum Aspiration Systems", 2020, 12(1), 72-76, Journal of Neurointerventional Surgery.
"JETi Thrombectomy System: Powerful Thrombectomy for the Toughest Peripheral Clot" Walk Vascular, Brochure in 4 pages. Accessed Mar. 11, 2024.
"Penumbra Indigo System Lightning 12" Brochure in 3 pages. Accessed Mar. 11, 2024. Penumbra, Inc. USA, www.penumbrainc.com.

* cited by examiner

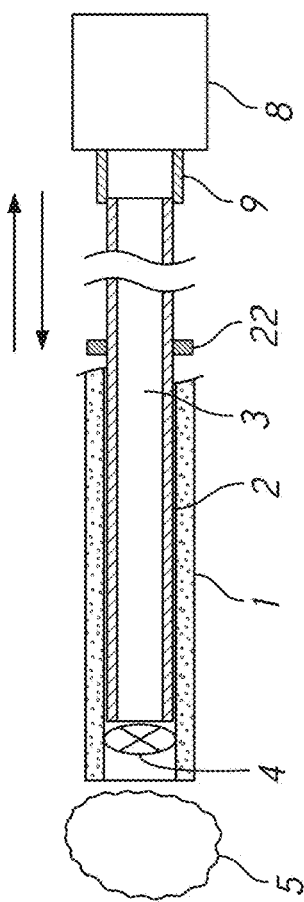
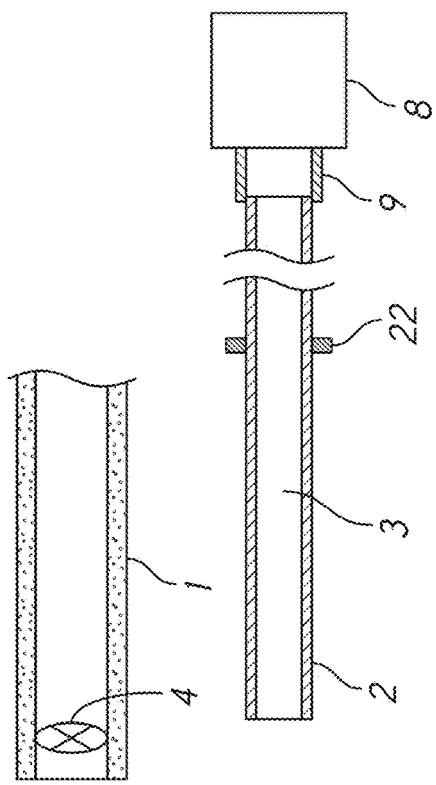
FIG. 8B
FIG. 8A

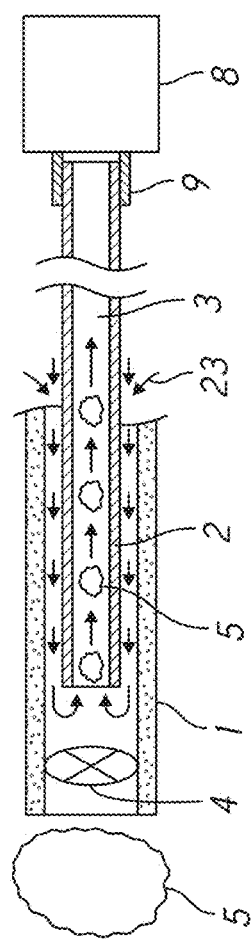
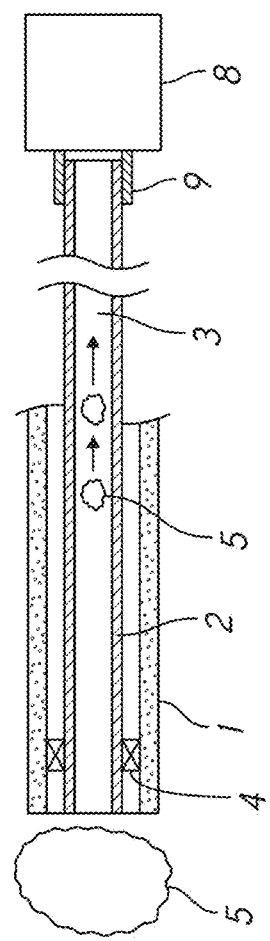
FIG. 9A
FIG. 9B

ASPIRATION CATHETER

INCORPORATION BY REFERENCE TO ANY PRIORITY APPLICATIONS

This application is a continuation of U.S. patent application Ser. No. 17/658,244, filed Apr. 6, 2022, titled "ASPIRATION CATHETER," which claims priority benefit of U.S. Provisional Application No. 63/200,995, filed Apr. 7, 2021, titled "DEVICE AND METHODS FOR AUGMENTED ASPIRATION" and U.S. Provisional Application No. 63/267,031, filed Jan. 21, 2022, titled "ASPIRATION CATHETER," which are hereby incorporated by reference in their entirety herein.

Any and all applications for which a foreign or domestic priority claim is identified in the Application Data Sheet as filed with the present application are hereby incorporated by reference under 37 C.F.R. § 1.57.

BACKGROUND

Field

The present disclosure relates to aspiration thrombectomy.

Description of the Related Art

Thromboembolism is a disease caused by blood clot formation. In the venous system, thromboembolism has two distinct peripheral manifestations—deep vein thrombosis (DVT) and pulmonary embolism (PE). Venous thromboembolism is a leading cause of death and disability worldwide and represents the third most common vascular diagnosis in the United States, after myocardial infarction and stroke. Researchers estimate that there are approximately one million venous thromboembolism patients in the United States annually, leading to 600,000 hospitalizations. This results in approximately 60,000-180,000 deaths in the United States, within the first 30 days, each year and an estimated venous thromboembolism-related direct health care costs exceed $10 billion per year.

Clots and their impact are, by their nature, heterogenous and unpredictable. Thrombi can have a variety of morphologies.

Arterial clots are subject to high flow rates and high shear forces. Clinically significant clots are typically found in vessels having a diameter of 1.5 mm to 7 mm. Arterial clots are soft, but overtime can become tough. As the clots get bigger and older, there is a diminishing response to blood thinners.

In contrast, peripheral venous clots are subject to lower flow rates and lower shear forces. Clinically significant venous clots can be typically found in vessels having a diameter of 3 mm to 25 mm. Pulmonary embolism clots are firmer and stickier compared to arterial clots and larger in volume. Blood thinners are risky because many pulmonary embolism patients are contraindicated. There is typically sub-optical response to systemic blood thinners due to clot size. Deep vein thrombosis has similar characteristics to pulmonary embolism and often adheres to vessel walls. Deep vein thrombosis can release clots leading to pulmonary embolism.

Due to the characteristics of the vascular system and clot morphology, by the time thromboembolism is diagnosed, the underlying clot can be significant in size and hardness due to age. As a result, methods designed to remove fresh, soft clots are inadequate and ineffective for removing the larger, older clots often associated with venous thromboembolism. Current products are cumbersome, and deliverability is, in many cases, compromised due to rigid catheters and complex mechanical components.

Of the population, 40-50% present with sub-massive and 5-10% present with massive pulmonary embolism. Clot size is often underestimated due to difficulties with contrast media flow in the presence of large clots. While blood thinners are able to mitigate risk of future clots, the use of such to remove clots typically takes a 12-24 hour long procedure and they are often unable to break down or eliminate existing blood clots and cause significant increase in bleeding risk to the patient.

SUMMARY

Aspiration thrombectomy is one of the standard endovascular treatments for removal of occlusive thrombi such as those which cause ischemic stroke, for example. During aspiration thrombectomy, an aspiration catheter (typically 90 cm to 165 cm in length and diameters adapted to the size of the treated blood vessel) is attached to a vacuum source at its proximal end and used to suck in thrombi at its distal end. The vacuum source creates a low-pressure area which in turn leads to suction forces. This is analogous to the use of a household vacuum cleaner's hose to suck in dirt and particles. Sometimes a syringe can be used to create vacuum.

Current thromboembolism solutions fail to provide an effective and repeatable approach to mechanical thrombectomy. Most mechanical thrombectomy systems are based faulty assumptions, for example a desire to provide a larger diameter catheter. But larger catheters lead to less deliverable and rigid catheter systems, clogging, and excess blood removal.

Moreover, current mechanical thrombectomy systems are designed to remove soft, young clots and encounter challenges when faced with larger clots that are older and harder. Conventional aspiration systems have difficulty with massive and sub-massive pulmonary embolism due to poor deliverability, clot geometry, clot volume, and clot composition. Thus, procedures using conventional systems significantly lengthen procedure time due to complicated procedural methods, multiple catheter removals to flush out clot, and manipulations to mobilize and aspirate the clot.

The current solutions for aspiration thrombectomy rely on entrainment forces which are much lower in magnitude than the aspiration forces predicted by simple calculations like Aspiration Force=(Blood Pressure−Vacuum Pressure)*Area. The aspiration force is often insufficient to fully draw in large or dense thrombi, which could become clogged in the distal tip of the aspiration catheter. To remove a thrombus which clogs the distal tip of the catheter, the doctor must pull the thrombus along with the catheter back along the catheter's entire introduction path, all the way out of the patient's body. This process is analogous to reeling a fish (the thrombus) out of a body of water with a hook on the end of a fishing line (the catheter). Then, once that piece of clot is removed from the tip, the catheter can be reinserted to continue the process and collect parts which were left behind.

When dealing with blood clots in the brain, time if of the essence and the therapeutic window for successful recovery is limited. The current aspiration method is slow and inefficient, and many times can cause particles to separate from the clot while it is being pulled out, potentially causing future embolization or blocking small blood vessels which in the case of ischemic stroke would lead to disability. Additionally, this method necessitates removing and reinserting a catheter multiple times, lengthening the total procedure time and increasing the risks of vessel damage and complications. These risks are especially high when aspiration thrombectomy is used to treat ischemic stroke but also exist when treating blood clots in the legs or in the venous system.

As mentioned above, the widespread belief and design practice is that aspiration force is a function of aspiration catheter cross sectional area and the pressure applied to the proximal end of the catheters. Both factors are limited and maxed out by current designs. Maximum theoretical vacuum pressure is limited to a theoretical negative 29.92 inHg at the pump (it is well known that the overall pressure differential is higher because of the blood pressure is higher than the atmospheric pressure) and the internal cross section of the aspiration catheter is ultimately defined by the size of the treated blood vessel. While veins and some peripheral arteries are relatively large in diameter (4-14 mm and more), distal blood vessel in the lower extremities are roughly 4 mm or less and brain arteries are typically in the range of 2.5 mm or less. Current aspiration pumps can only reach 80%-95% of the maximum vacuum pressure and catheter technology improved in a way that thin wall aspiration catheters could have wall thickness as low as 0.1 mm maximizing its cross-sectional area sometime slightly improved using beveled tips. Those limitations brought the field to a dead end, where treatment is still sub-optimal and improvements are limited by the laws of physics governing steady state pressure differential. On top of this, the vacuum pressure drops rapidly along the length and curves of the aspiration catheter when placed in the human anatomy and some measurements show that the vacuum pressure at the tip of the catheter, seconds after the pump is turned on, near the clot where it is most needed, could be as low as 10 inHg, sometimes even 3-5 inHg rendering aspiration highly ineffective in providing fast and complete removal of the clot. Attempts were made to use oscillating vacuum pumps to increase the aspiration efficiency by slowly "fatiguing" the blood clot, but those methods have not become the standard of care due to marginal improvements and difficulties with large and more challenging clots. In fact, those methods may even increase the total aspiration time since the vacuum pump is moving from 29.92 inHg to a lower pressure and back up (to create the pulses) thus the average is below maximum. It may also contribute to distal embolization due to the pulsatile nature. The force generated by those methods is limited by the max vacuum force which is the only energy supplied to the system and creating force.

In the absence of total blockage of flow, the pressure at the distal end of the catheter (static or pulsatile) will never come close to the pressure applied to the proximal end of the aspiration (near the vacuum source) due to losses in the small diameter aspiration tube and dampening effect of the liquids and particles already in the tube. In practice, as mentioned above, the distal pressure is only slightly lower than the pressure of the fluid surrounding the aspiration tip (beyond the blood pressure differential), resulting in weak aspiration force and large dampening effect that further contribute to inefficiencies. This is analogous to the pressure profile in a long pipe with a pump at one end. Due to friction and dampening forces, the pressure keeps dropping along the length of the pipe and in each curve or directional change of the pipe. In aspiration thrombectomy, this pressure loss is caused by the small aspiration lumen radii and the tortuous human blood vessels anatomy, which are necessary to fit the catheter within small vessels.

The force which aspirates the thrombus in standard aspiration thrombectomy is the drag force between the blood flowing into the catheter tip and the thrombus, otherwise known as entrainment force. Entrainment forces, like drag, are a function of fluid flow rate. The distal pressure only approaches the pressure exerted by the vacuum source when the distal tip is totally blocked, stopping blood flow and allowing distal vacuum pressure to build. However, to reach this level of blockage, the thrombus must be stuck in the distal tip, blocking any additional aspiration and practically leading to malfunction.

Current thromboembolism removal solutions in the market fail to provide an effective and repeatable approach to mechanical thrombectomy. No currently marketed device provides a complete, effective and predictable solution in the venous, peripheral or neurovasculature. The aspiration catheter systems described herein address the clinical need and are designed to overcome many of the limitations of currently marketed products. The systems described herein address peripheral clot removal efficacy regardless of age, size (length and diameter), solidness, or location, with a lower bleeding risk.

One or more features described herein contribute to these improved results. For example, the aspiration catheter systems described herein maintain maximal aspiration force at the distal tip (e.g., at least about 90% of vacuum pressure at the vacuum source, or at least about 95% of vacuum pressure at the vacuum source, or at least about 98% of vacuum pressure at the vacuum source, or at least about 99% of vacuum pressure at the vacuum source). The valve assembly described herein enables pressure to build up at the distal end of the catheter assembly, thereby improving clot acquisition when the valve opens. Resistance can be decreased by exploiting physical weaknesses in the clot structure. Because clots are five times less resistant to shear forces compared to tensile forces used in conventional aspiration, shear forces can be used to segment the clot to decrease the clot length and friction.

In some embodiments, the aspiration catheter system may provide simultaneous irrigation flow to minimize clogs and obstruction during the procedure. The water pressure column can increase pressure within the catheter assembly beyond the maximum theoretical vacuum pressure supplied by the vacuum source alone. This self-cleaning mechanism results in the clearance of clots without the need to remove the device during the procedure. Using these features, the aspiration catheter system can remove large clots in less time and without removing or manipulating the catheter system.

In some embodiments, the aspiration catheter system can include a dual catheter design with an outer support catheter and an inner aspiration catheter. One or both catheters can have a braided and/or coils reinforcement with an atraumatic tip making it easier to navigate the vasculature.

The aspiration catheter may be operably connected to any vacuum source. Unlike current thrombectomy approaches that use pulsatile vacuum, the vacuum source can apply a constant or continuous vacuum throughout the procedure. There are no valves in the vacuum source or at the proximal end of the catheter assembly for modulating vacuum pressure. Instead, the catheter assembly decreases pressure loss along a length of the aspiration catheter assembly, thus amplifying clot removal forces. For example, the support catheter can include a valve in a distal portion of the support catheter. When the valve is closed, pressure can build up at the distal end of the catheter assembly. When the valve is open, the aspiration catheter can aspirate at least a portion of the clot. Using shear forces, the aspiration catheter assembly can break the clot into smaller pieces and limit clogging. These features make the catheter assembly suitable for all clot types. Limiting clogging reduces the number of exchanges, thereby making the procedure less labor intensive and faster. Moreover, periodically closing the valve minimizes blood loss through the aspiration catheter while further increasing shear forces.

Valve control can be manual or automated. In an automated system, safety features can be built in to stop aspiration when noncontinuous aspiration is detected. Moreover, the system can collect inputs regarding clot characteristics or catheter performance to change valve control and optimize aspiration.

Optionally, the support catheter can be operably connected to an irrigation source, for example to provide a saline flush during aspiration. The irrigation can flow distally within a space between the support catheter and the aspiration catheter, flow into the distal end of the aspiration catheter, and flow back proximally out of the aspiration catheter towards the vacuum source. The irrigation flow can facilitate aspiration and minimize clogs. This reduces the need to separately flush the catheter during the procedure. The irrigation can be continuously provided during the thrombectomy procedure and independent of the vacuum applied. There are no valves in the irrigation source or at the proximal end of the catheter system to modulate the irrigation flow. The irrigation source can be pressurized (for example by using a pressure pump, pressurized or elevated saline bag) to further increase the overall pressure differential. Without such system, the maximum theoretical pressure differential is the pressure provided by the vacuum source plus (minus) the blood pressure. Therefore, it is approximately 1 bar with some margins due to blood pressure. The current system enables increasing this pressure differential substantially, potentially multiply the pressure differential by providing a pressurized irrigation source. Such pressure is additive to the vacuum pressure during the backflow irrigation cycle.

Certain aspects of the disclosure are directed toward an aspiration catheter assembly for removing a clot. The aspiration catheter assembly can include a support catheter configured to be in fluid connection with an irrigation source and an aspiration catheter configured to be in fluid connection with a vacuum source. The aspiration catheter can be disposed within the support catheter and be capable of moving relative to the support catheter. The aspiration catheter can include an aspiration lumen for receiving at least a portion of the clot. The aspiration catheter assembly can include a valve for controlling a level of vacuum at a distal end of the aspiration catheter assembly and/or preventing irrigation flow out of the distal end of the aspiration catheter assembly. For example, the support catheter can include a single valve for controlling a vacuum at a distal end of the aspiration catheter assembly and/or preventing irrigation flow out of the support catheter. In some embodiments, the valve opens when the aspiration catheter is advanced through the valve, and the valve closes when the aspiration catheter is retracted proximal of the valve.

The support catheter can include an elongate tubular body and a valve at or near a distal end of the support catheter, for example within 5 cm from the distal end of the support catheter, within 1 cm from the distal end of the support catheter, within 0.5 cm from the distal end of the support catheter, or at the distal end of the support catheter. The valve can be a one-way valve, for example a slit valve, a valve with leaflets, or a valve with a protruding portion like a duckbill valve. The valve can include an edge surrounding the valve opening that is sufficient to disrupt a clot. The valve can control a level of vacuum pressure at a distal end of the aspiration catheter assembly by allowing pressure to build when the valve is closed. The valve can also prevent irrigation fluid from flowing out of the support catheter when the valve is open and/or closed.

In some embodiments, the support catheter can include a valve housing secured to a distal end of the elongate tubular body. The distal end of the valve housing can be at a distal end of the support catheter. The distal end of the valve housing can be tapered. The valve housing can be positioned radially outward of the elongate tubular body and secured to an exterior surface of the elongate tubular body. But in other configurations, the valve housing may be inserted into the elongate tubular body. The valve can be disposed within the valve housing. The distal end of the support catheter, which may be the valve housing, can form a breaking shoulder to tear the clot.

The aspiration catheter can include an aspiration lumen for receiving at least a portion of the clot. In some embodiments, a working length of the aspiration catheter can be at least as long as a working length of the support catheter. In other embodiments, a working length of the aspiration catheter can be less than a working length of the support catheter. Movement of the aspiration catheter relative to the support catheter can be limited by a stopper on the support catheter and/or the aspiration catheter.

Any of the catheter assemblies described herein can include a manifold at a proximal portion of the aspiration catheter assembly. The manifold can be secured to a proximal end of the support catheter. The aspiration catheter can extend proximally of the manifold for connection to the vacuum source. The manifold can include an inlet for irrigation fluid. The manifold can include a seal member to form a seal against the aspiration catheter and prevent fluid in a space between the support catheter and the aspiration catheter from flowing out of the proximal end of the manifold.

The movement of any of the catheter assemblies described herein may be manual or automatic. When automatic, the aspiration catheter assembly can include a drive unit that can be attached to or integrated with the aspiration catheter. The drive unit can include a motor to be operably connected to the aspiration catheter. The catheter assembly can include a controller in the drive unit or separate from the drive unit. The controller can cause the motor to advance and retract the aspiration catheter relative to the valve of the support catheter according to a preselected pattern or in response to particular parameters of the clot or performance of the aspiration catheter assembly.

The catheter assemblies described herein can form a part of an aspiration catheter system including a vacuum source. The vacuum source can be in communication with the aspiration catheter to apply constant vacuum through the aspiration lumen. The applied vacuum pressure can be constant and continuous.

The catheter assemblies described herein can form a part of an aspiration catheter assembly including an irrigation source. The irrigation source can deliver irrigation fluid distally through a space between the support catheter and the aspiration catheter. When the aspiration catheter extends through the valve, a seal between the aspiration catheter and the valve can prevent irrigation fluid from flowing out of the distal end of the support catheter. When the aspiration catheter is retracted through the valve, the valve can prevent irrigation fluid from flowing out of the distal end of the support catheter.

Certain aspects of the disclosure are directed toward a method of removing a clot using an aspiration catheter assembly including any of the features described herein. The method can include applying vacuum at a proximal portion of the aspiration catheter assembly. The applied vacuum can be constant and continuous throughout the removal of the clot. The method can include opening and blocking flow at the distal portion of the aspiration catheter assembly. This step can be performed by opening and closing a valve, for example by advancing and retracting the aspiration catheter relative to a distal end of the support catheter. The method can include repeatedly opening and blocking flow at the distal portion of the aspiration catheter assembly to remove the clot, for example at least 2×, at least 5×, or at least 10× per second. Flow can be opened and blocked for different periods of time. Flow can be opened for longer time periods than flow is blocked. For example, flow can be blocked for at least about 0.05 seconds (or at least about 0.1 seconds, or at least about 0.25 seconds, or at least about 0.5 seconds) and flow can be opened for no more than about 1 second (or no more than 0.5 seconds, or no more than 0.25 seconds, or no more than 0.5 seconds). The steps of opening and blocking flow can be performed manually or automatically.

When flow is open at the distal portion of the aspiration catheter assembly, the aspiration catheter assembly can aspirate at least a portion of the clot through an aspiration lumen of the aspiration catheter assembly. When flow is blocked at the distal portion of the aspiration catheter assembly, vacuum pressure increases at the distal portion of the aspiration catheter assembly. For example, absolute pressure at the distal portion of the aspiration catheter assembly can be at least about 15 inHg (or at least about 20 inHg, at least about 25 inHg, at least about 30 inHg) where a diameter of the aspiration lumen is between 1 mm and 3 mm. Vacuum pressure at the distal portion of the aspiration catheter system can be at least about 50% of vacuum pressure (or at least 80%, or at least 85%, or at least 90%, or at least 95%) applied at the proximal portion of the aspiration catheter.

Certain methods can include applying vacuum to an aspiration catheter and delivering irrigation fluid through a space between the aspiration catheter and a support catheter with the aspiration catheter extending through the support catheter. The method can include advancing the aspiration catheter distal of the support catheter to aspirate at least a portion of the clot through an aspiration lumen of the aspiration catheter and retracting the aspiration catheter to block fluid flow at a distal end of the support catheter. This step can be performed repeatedly to remove the clot. The applied vacuum can cause the irrigation fluid to flow from the space between the aspiration catheter and the support catheter and into the distal end of the aspiration catheter. This can propel clots through the aspiration lumen. In some methods, the flow of irrigation fluid may be constant during opening and blocking of flow. In other methods, the flow of irrigation fluid may be intermittently turned off when flow is open at the distal end of the aspiration catheter assembly.

Any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No individual aspects of this disclosure are essential or indispensable.

BRIEF DESCRIPTION OF THE DRAWINGS

Various embodiments are depicted in the accompanying drawings for illustrative purposes and should in no way be interpreted as limiting the scope of the embodiments. Furthermore, various features of different disclosed embodiments can be combined to form additional embodiments, which are part of this disclosure.

FIG. 1A shows the aspiration catheter moving towards the closed distal valve. FIG. 1B shows the distal valve open and the aspiration catheter grabbing the thrombus. FIG. 1C shows the aspiration catheter retracting back into the support catheter, breaking off a piece of thrombus. FIG. 1D shows the broken off piece of thrombus being aspirated while the aspiration catheter is behind the closed valve.

FIGS. 8A and 8B show a cross section of an aspiration catheter and the support catheter. FIG. 8A shows an exploded view and FIG. 8B shows an assembly view.

FIG. 9A shows a cross section of a system wherein fluid is allowed to enter the gap between the support catheter and the aspiration catheter so that thrombus will be continuously aspirated through the aspiration lumen, even when the distal valve is closed.

FIG. 9B shows the same embodiment in the active phase without flow between the support and aspiration catheters.

DETAILED DESCRIPTION

The present disclosure provides devices for the treatment and removal of thrombus in blood vessels through aspiration thrombectomy to address the challenges outlined above and significantly enhance the ability to remove blood clots. Certain aspects of the disclosure are directed toward a device for aspiration thrombectomy with a valve apparatus that significantly improves the transmission of vacuum pressure from the proximal end of an aspiration lumen, to the distal end of the aspiration lumen, thus reducing or eliminating the dampening effect which is the pressure drop gradient between the vacuum pump and the tip of an aspiration catheter (usually 90 cm to 165 cm long or more depending on the target anatomy and certain accessories). The valve apparatus may be located at a distal end of the catheter system. In this scenario the aspiration catheter is subject to vacuum without any longitudinal and temporal dampening effects which impede current products. The system enables the application of instantaneous, short distance, transient force effect applied directly to the blood clot by utilizing an active distal valve apparatus without significantly compromising the catheter lumen (which contributes to the steady state pressure difference). This can be done without pulsating flow at the pump or otherwise varying flow at a proximal portion of the aspiration catheter system. For example, the pump may operate at a constant flow rate.

The aspiration catheter assembly can include two components operating in concert—(1) valved support catheter and (2) inner vacuum aspiration catheter that fits inside the valved support catheter and capable of fast relative movement, either manual or automatic. The valved support catheter can include a valve apparatus placed close to or at the distal end of a support catheter with a recess from the distal tip, allowing the support catheter distal end zone to serve as the thrombus breaking shoulder. For example, the valve apparatus may be positioned within 15 cm, within 10 cm, within 5 cm, within 1 cm, within 0.5 cm, or less of the distal end of the support catheter.

Figure 1B:
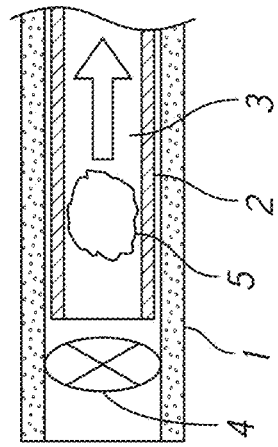
FIGS. 1A to 1D show an aspiration catheter cycling out of and back into a distal valve.
Figure 1A:
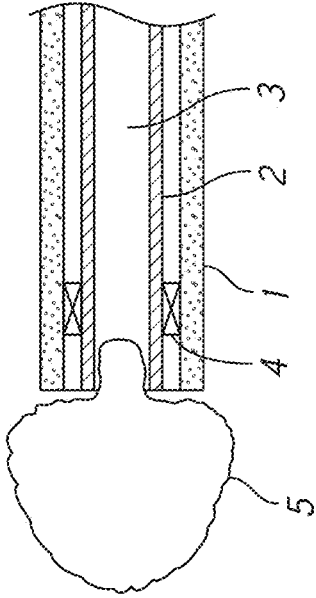
Figure 1D:
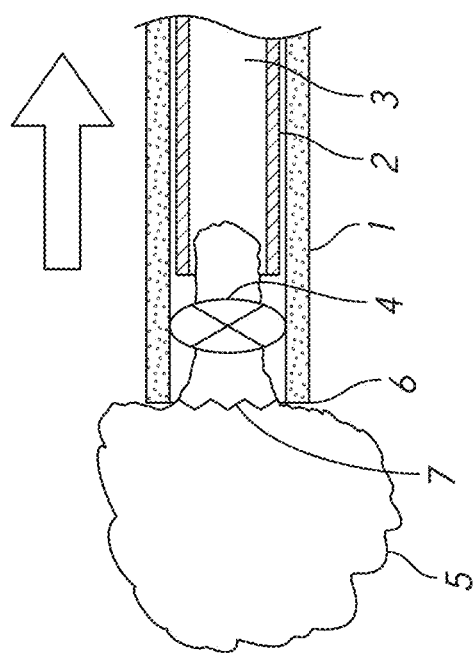
Figure 1C:
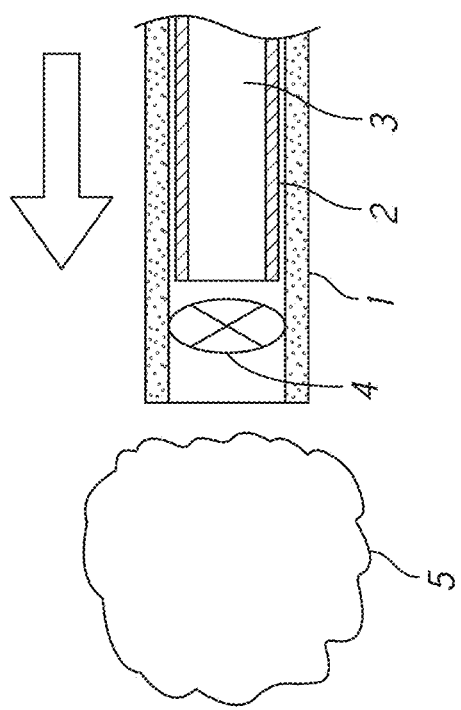

As shown in FIGS. 1A to 1D, the catheter assembly comprises an aspiration catheter 2 which is contained within a support catheter 1 and moves distally toward a valve 4 (FIG. 1A) to grab onto a blood clot 5 (FIG. 1B) when the aspiration catheter 2 opens the distal valve 4. As shown in FIG. 1C, the aspiration catheter 2 is then retracted back behind the valve 4, stretching the clot 5 between the aspiration catheter 2 and the outer wall of the support catheter 1 (or a component of the support catheter 1), here referred to as the thrombus breaking shoulder 6. The shoulder 6 may be an edge of the aspiration catheter 2 and/or the support catheter 1. The clot 5 breaks along the thrombus breaking line 7. FIG. 1D shows the broken off piece of clot 5 being aspirated while the aspiration catheter 2 is behind the closed valve 4.

As shown in FIGS. 1A to 1D, the distal area of a support catheter 1 may contain a valve 4. The distal area may be within 15 cm of the distal tip of the support catheter, within 10 cm of the distal tip of the support catheter, within 5 cm of the distal tip of the support catheter, within 1 cm of the distal tip of the support catheter, or at the distal tip of the support catheter. An aspiration catheter 2 can be actuated through, for example pushed through, the valve 4, poking out of and tucking back into the support catheter 1. Pushing the aspiration catheter 2 can open the valve 4 outwards. This can form a seal between the valve 4 and the aspiration catheter 2. In other configurations, the aspiration catheter can be initially located outside of the valve and open the lumen by pulling the valve inwards. Optionally, the aspiration catheter tip may be beveled so that as it pokes through the valve it applies greater force to the clot. The aspiration catheter and/or the support catheter may contain side holes to enable the aspiration catheter to direct aspirate towards its sides. This will help keep the thrombus from becoming stuck around and over the distal tip. The aspiration catheter can be similar in length or longer than the support catheter but can also be constructed using a short (1 cm-5 cm or more) distal segment actuated by a push wire.

This system operates as a "grab and pull" combination in which the continuous vacuum in the aspiration lumen 3 and, when the aspiration catheter 2 protrudes outside of the valve 4 of the support catheter 1, the aspiration catheter 2 "grabs" the blood clot allowing resistant clots to get "stuck" and jam the vacuum aspiration lumen 3 because the vacuum force may not be strong enough to deform or break the clot and is lower than the clot maximum resistance force (see FIG. 1B). At that point, the aspiration catheter is rapidly pulled back proximal of the valve (see FIG. 1C), and a mechanical pulling force is added to the vacuum force thus increasing the maximum force applied on the thrombus above the maximum force that can be generated by the vacuum pump (Total Force=Vacuum Aspiration Force+Rapid Pullback Force). This combination creates a combined force greater than the clot maximum resistance force, thus splitting the clot at the breaking shoulder of the support catheter distal tip designed to be sufficiently rigid to allow the clot to break. The rapid pull back has another significance since blood clots are viscoelastic in nature thus responding to speed of loading and not just to the total force. Rapid pull back can break the viscoelastic clot material using less force that slow or quasistatic force application. The breaking shoulder contributes to a three-dimensional stress field applied on the clot enabling creation of tensile and shear strains that otherwise do not exist in the same way in other aspiration systems (which is why aspiration attempts commonly fail "single pass" clot removal when dealing with resistant clots). The mechanical pull force and the shear forces from the breaking shoulder augment the maximum force that can be generated by the aspiration vacuum pump by adding a mechanical pulling component that cannot be otherwise created by a vacuum pump (continuous vacuum or pulsatile vacuum). Once the aspiration catheter passes the valve on its way in, the valve is sealed and the clot piece that was teared by the stress field is subject to maximum vacuum and aspirated to the proximal end of the device and out of the body. This is described in more detail with respect to FIGS. 2 and 3 below.

Once the aspiration catheter 2 is pulled inside the valve 4, the aspiration is converted to vacuum that "charges" the aspiration catheter 2, bringing the vacuum all the way to the tip of the aspiration catheter thus bypassing dampening effects of the tube and the tortuous anatomy. The aspiration catheter 2 is then pushed out and the process continues. This allows for a vastly improved outcome which includes the ability to break resistant clots and reduce treatment time.

Figure 2:
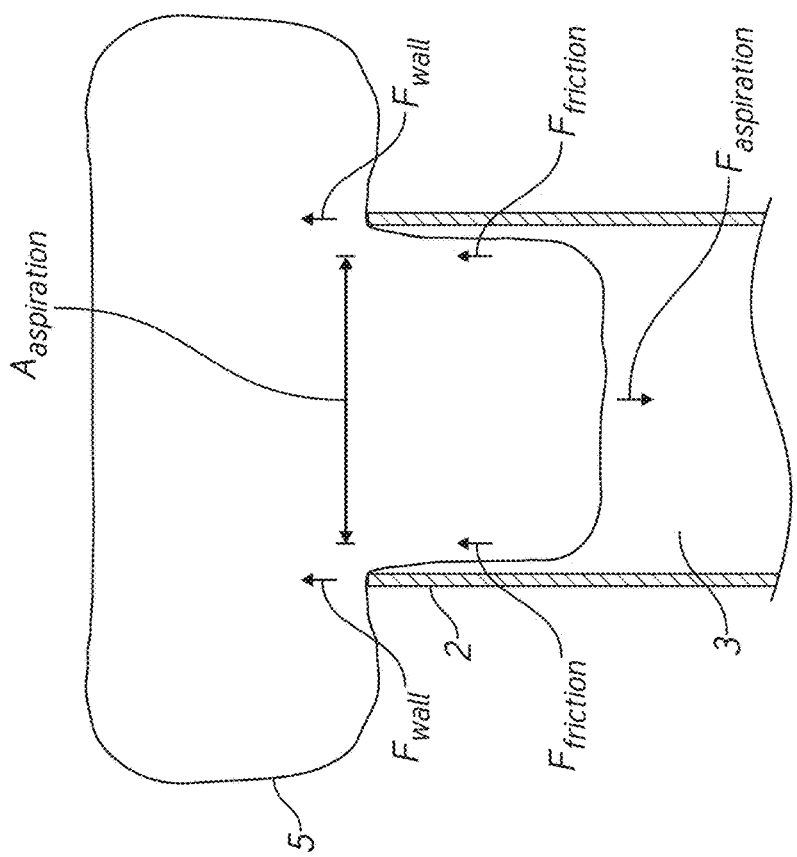
FIG. 2 depicts the simplified mechanics of a clogged aspiration catheter.

In the traditional aspiration catheter, thrombus clogs happen because the aspiration force is insufficient to continue extruding more thrombus into the aspiration lumen or break off the piece of thrombus within the aspiration catheter from the rest of the thrombus (see FIG. 2). However, in the systems described herein, as the aspiration catheter is poked out of and back into the sealing valve, the force used to retract the aspiration catheter back behind the membrane will add to the aspiration force applied to the thrombus. When added together, these forces are sufficient to break the aspirated piece off the rest of the thrombus, preventing a clog and freeing up the aspiration lumen to take in more thrombus (see FIG. 3).

A more fibrin rich and crosslinked thrombus could clog up any conventional aspiration catheter regardless of the vacuum source parameters (continuous or pulsatile) and prevent any further fluid flow or aspiration to the point that the entire system must be removed from the body, slowing down the treatment time substantially and increasing the risk of distal embolization. These clogs have been referred to in the art as extrusion clogs because the thrombus elongates and takes on the shape of the aspiration lumen as it is sucked towards the proximal end of the aspiration catheter. These extruding thrombus segments become clogged because even the maximum vacuum pressure differential does not supply sufficient energy to break and separate the thrombus. FIG. 2 depicts the simplified mechanics of a clogged aspiration catheter 2. In pure aspiration thrombectomy, the aspiration force is less than the force required to break the thrombus. This results in the thrombus 5 becoming stuck in the tip of the aspiration catheter 2, preventing full aspiration and slowing treatment.

Figure 3:
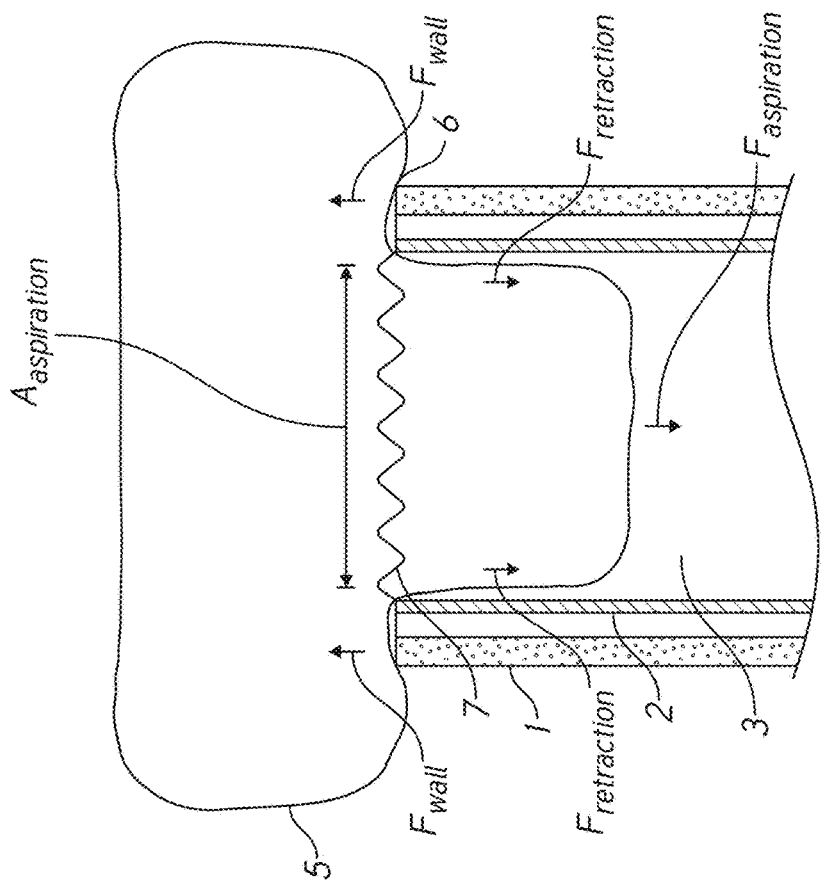
FIG. 3 depicts the simplified mechanics of an aspiration catheter preventing clogs during aspiration by splitting off smaller pieces of thrombus.

In the systems described herein, these clogs are prevented by increasing the maximum force well above the maximum force that can be generated by the pressure gradient of any vacuum aspiration pump (all are limited by the theoretical maximum pressure differential). This allows breaking and separating the clogs and prevention of aspiration jamming by reducing the volume of the pieces of thrombus which are being aspirated. FIG. 3 depicts the simplified mechanics of an example system of the present disclosure preventing clogs during aspiration by splitting off smaller pieces of thrombus 5. The retraction force used to retract the aspiration catheter 2 adds to the aspiration force via friction applied to the thrombus 5 at its contact area with the aspiration catheter 2. The summation of these two forces is sufficient to exceed the thrombus yield stress, causing a smaller piece of thrombus to split off from the larger mass. This smaller piece can then be aspirated successfully while the aspiration catheter is moving forward to grab another piece of thrombus, starting the cycle again.

This thrombus breaking function only occurs within the support catheter, so the broken pieces of thrombus have minimal possibility of being released in the vasculature as smaller emboli. This is further supported by the "vacuum charging valve" that enable full vacuum in the aspiration catheter with no dampening effects and provide a significant force kick (vacuum force surge) when the aspiration catheter protrudes through the valved support catheter. When charged, vacuum at the distal end of the aspiration catheter can be at least about 90% of vacuum supplied by the vacuum source, at least about 95% of vacuum supplied by the vacuum source, at least 98% of vacuum supplied by the vacuum source, or at least 99% of vacuum supplied by the vacuum source. Combined with the ability to break the clot, the treatment time is reduced. Without the valve, the system would still break resistant clots, but treatment times could be longer since the dual catheter system has smaller cross section compared to a single catheter system. The volume flow rate of a fluid passing through a smaller cross-sectional area is inherently smaller and the vacuum charging valve well compensate for the smaller cross section.

With a 3.5 cm long and 7.5 mm diameter clot, a 1 mm diameter aspiration lumen, and 24 inHg of vacuum pressure applied to the proximal side of the aspiration catheter, clot removal time is 2.5 min without the valve and 1.5 min with the valve. With the dual catheter assembly described here, the clot breaking shoulder can remove resistant clots by leveraging the added mechanical force component. The distal edge of the support catheter 1 and/or the aspiration catheter 2 can be sufficient rigid to break the clot. There is at least a 40% treatment time reduction measured in the lab model due to the valve, which for some procedures may result in a life changing outcome for the patient. Further time reduction of at least 10% can be achieved by using the self-cleaning cycle depicted in FIGS. 9A and 9B.

The valves described herein can be made of one or more layers of polymer such as silicone but can also be made of other materials including thin nitinol or flexible metal, ethylene-vinyl acetate, polyurethanes, PTFE, nylon or Pebax certain fabrics or composites and in some cases biological tissue. The valve design provides enough rigidity to stop fluid flow when the aspiration catheter is retracted and enough compliance to allow the tip of aspiration catheter to be exposed to the blood. The leaflets of the valve may be cut into slits, triangles, semicircles, or some other shape. Leaflets may overlap one another to ensure the creation of a good seal when the valve is closed. The valves may be between 0.05 and 2.0 mm thick, for example between 0.1 and 1.0 mm thick. The leaflets may be reinforced with stiffer wires or fibers made of stainless steel, nitinol, or a harder polymer. The valve may have between 2 and 10 leaflets, for example between 3 and 8 leaflets. The valve may be within the distal region of the support catheter, or it may be recessed within the distal tip of the support catheter by up to 10 mm and in some cases no more than 100 mm depending on the target blood vessel (head, neck, legs, or veins). The valve may be recessed within the distal tip of the support catheter by between 1.0 mm and 10.0 mm. The recessed valve may have a portion of the support catheter extending distally to the distal face of the valve. Thrombus will be aspirated into the aspiration catheter as it is extended beyond the distal end of the support catheter and then the thrombus will be pulled against the distal end of the support catheter as the aspiration catheter is retracted, creating a 3D stress field which includes shear and tensile stresses which contribute to breaking off the aspirated piece of thrombus. This portion of the support catheter therefore creates a thrombus breaking shoulder which drastically improves aspiration efficacy. The recessed valve also prevents the aspiration catheter from poking into the walls of the vasculature when it is exposed through the valve, making the apparatus safer.

Silicone has great resistance to fatigue and is able to seal well over many cycles of aspiration catheter insertion and retraction. The valve may be thermally bonded or mechanically fixed within the shaft of the support catheter.

Figure 6B:
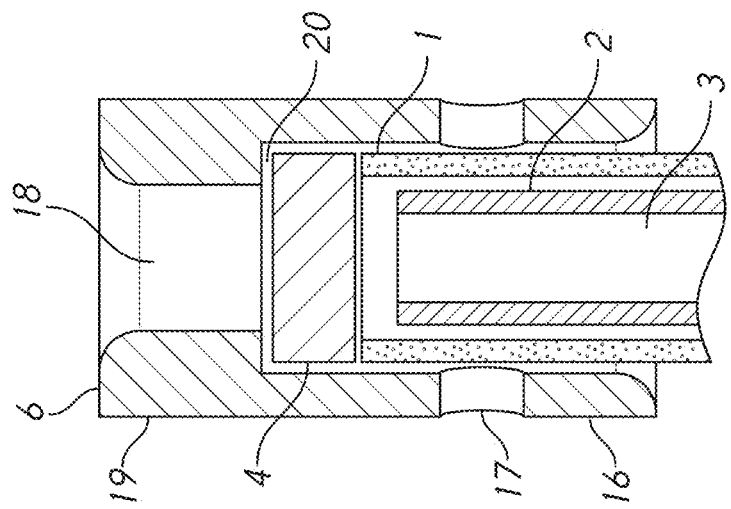
FIGS. 6A and 6B show a cross section of a distal cap apparatus used to fix a valve to the support catheter.
Figure 6A:
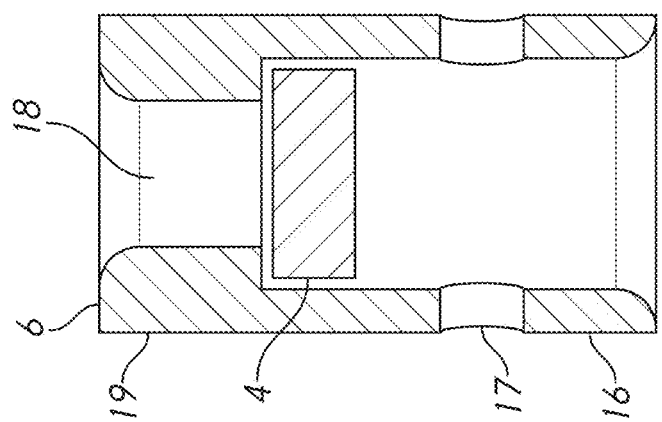

In some embodiments, the silicone valve can be fixated within the aspiration tip by inserting the distal tip of the support catheter and the silicone valve into a valve fixation cap (also referred to herein as a valve housing). The valve can be held in place by cap material radially and/or distally. The valve can be held in place by the support catheter proximally. In this way, the valve can have material on each side, enabling its mechanical fixation. FIG. 6A and FIG. 6B show a schematic cross-section of this configuration. The valve may be exposed to the aspiration lumen up to a certain radius and supported by material proximally and distally beyond that radius by a valve-supporting lip of material. For neurovascular applications, the radial thickness of this valve-supporting lip can be between 0.1 mm and 1.0 mm, for example between 0.1 mm and 0.3 mm, varying with the overall valve diameter. For peripheral or vein applications the dimensions can be larger. The outer diameter of the fixation cap may be equivalent to the outer diameter of the support catheter. In this case, the support catheter can be swaged to allow the valve fixation cap to be bonded on without increasing the overall outer diameter of the distal tip.

FIGS. 6A and 6B show a cross section of a configuration wherein a valve housing 16 is used to fix a valve 4 to the support catheter 1. FIG. 6A shows only the valve housing 16 and the valve 4. FIG. 6B shows the aspiration catheter 2 and support catheter 1 inserted into the valve housing 16. The support catheter 1 may be fixated to the valve housing 16 by the use of adhesive applied through holes 17 in the valve housing 16. The valve 4 may be held in place by material on either side which may form cap-supporting ridges 20. The valve housing 16 may contain a distal wall 19 which may create a gap 18 between the distal tip of the valve housing 16 (or the aspiration catheter system) and the valve 4. This gap 18 holds the thrombus 5 at a distance from the valve 4 during aspiration and the walls of the valve housing 16 form a thrombus-breaking shoulder 6.

Figure 7:
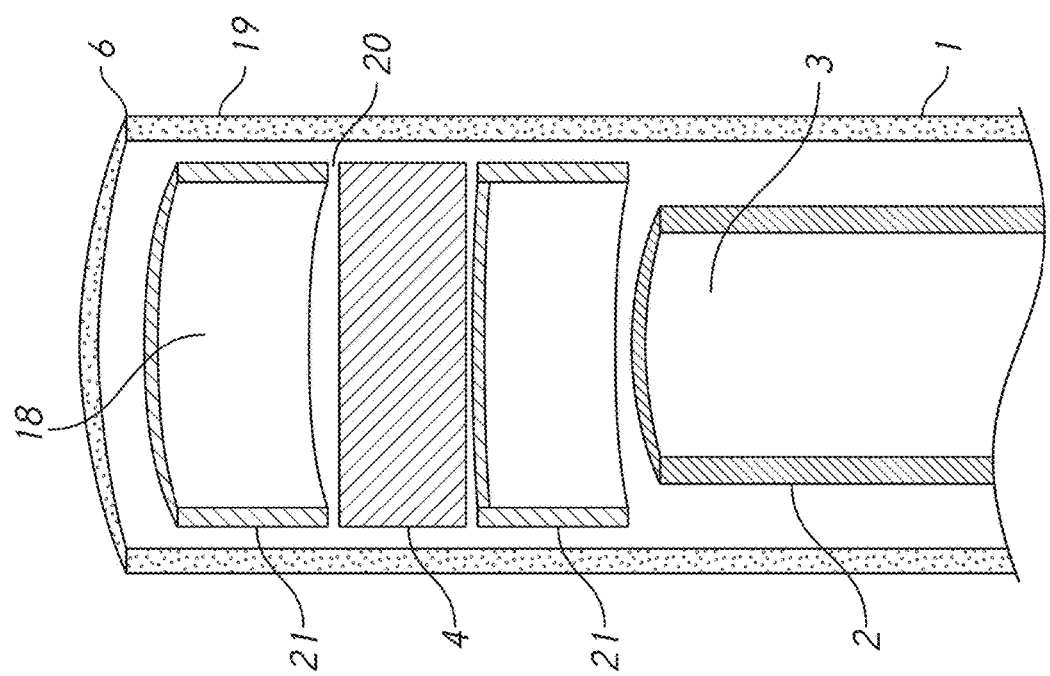
FIG. 7 shows a cross section of another system wherein valve fixation material is thermally bonded within the support catheter on either side of the valve, fixing the valve to the support catheter.

In some embodiments, the valve can be fixated within the aspiration tip of the support catheter by embedding the valve between two pieces of valve fixation material which can be thermally bonded within the distal tip of the support catheter. FIG. 7 shows a schematic cross-section of this configuration. FIG. 7 shows a cross section of an alternate to the valve housing in which valve fixation material 21 is thermally bonded within the support catheter 1 on either side of the valve 4, fixing the valve 4 within the support catheter. The valve may be exposed to the aspiration lumen up to a certain radius and supported by material proximally and distally beyond that radius by the valve fixation material, which will in effect embody a valve-supporting lip of material. The radial thickness of this valve-supporting lip may be between 0.1 mm and 1.0 mm, for example between 0.1 mm and 0.3 mm, varying with the overall valve diameter. The valve supporting material may include polymers such as silicone or nylon or other known polymers and materials including metals such as nitinol and certain elastic alloys and composite materials or fabrics.

Both the aspiration catheter and support catheter may be lined with Teflon or some other material for enhanced lubricity. Making the aspiration catheter or parts of it from a more rigid material such as braided metal would make it easier to actuate through the distal valve. The aspiration catheter may be the same length as the support catheter, or it may be shorter than the support catheter (see FIG. 5) and in most cases longer than the support catheter with a connection to the vacuum pump (see FIG. 4). The aspiration catheter may be actuated back and forth through the valve manually or automatically.

Figure 4:
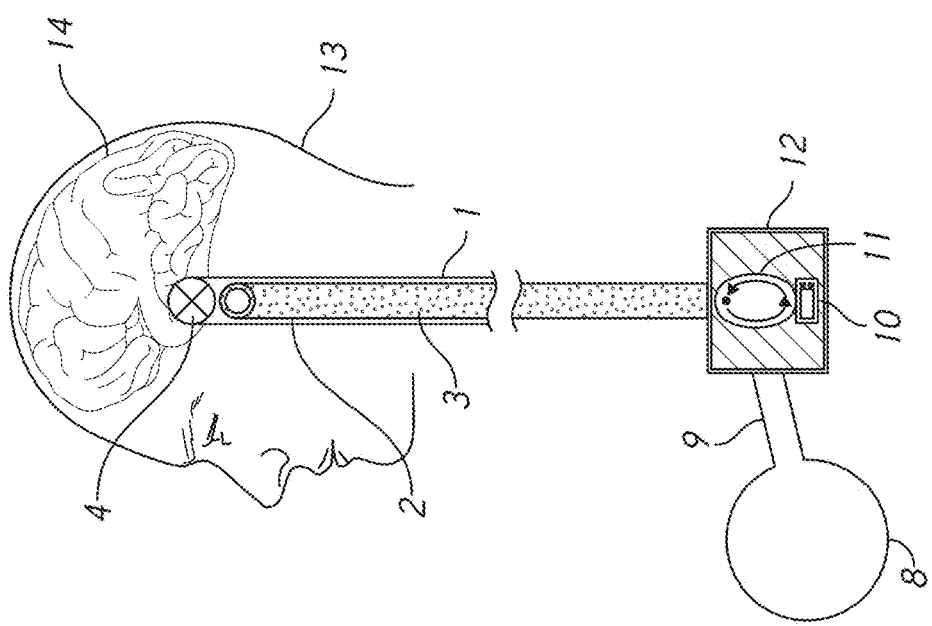
FIG. 4 shows an overall schematic view of an aspiration catheter extending through the support catheter.

FIG. 4 shows an overall schematic view of a configuration wherein catheter assembly extends through the head 13 to the neurovasculature 14. The aspiration catheter 2 extends through the whole length of the support catheter 1. A vacuum source 8 may be attached to the catheter hub 12 (also referred to herein as a manifold) via aspiration source tubing 9. In some embodiments, the hub 12 may contain or be operably connected with a battery 10 and a cam shaft with motor 11. This motor 11 automatically moves the aspiration catheter 2 out of and back into the valve 4.

Figure 5:
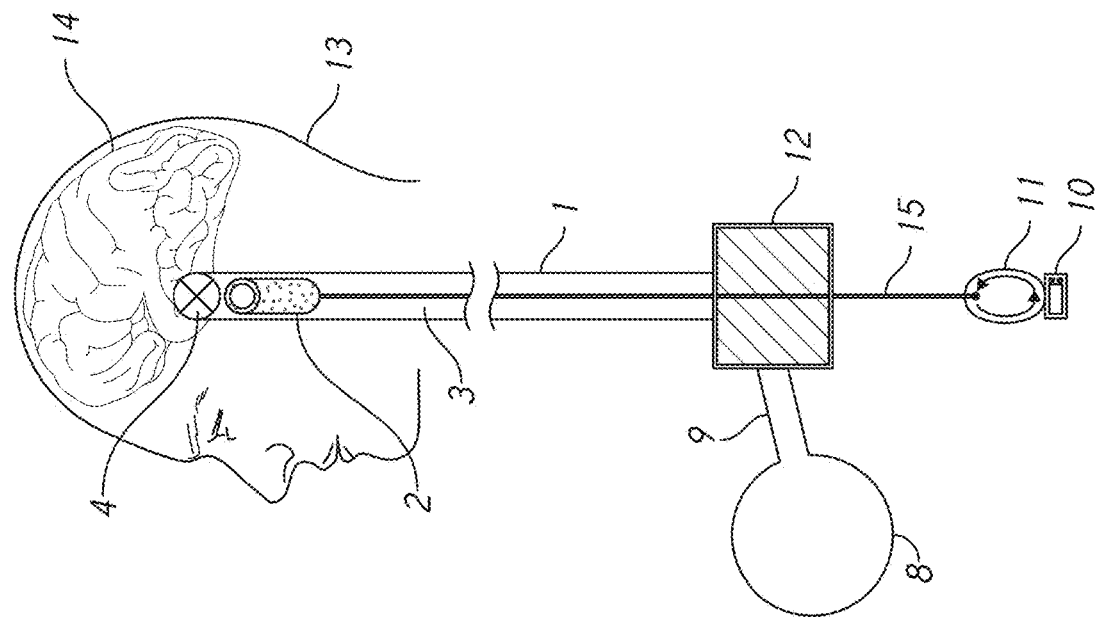
FIG. 5 shows an overall schematic view of another aspiration catheter extending through a portion of the support catheter and actuated by a push wire which running a remaining length to the proximal end of the support catheter.

In some embodiments and as shown in FIG. 5, the aspiration catheter is shorter than the support catheter, and is attached to a metal wire or mandrel which can run to the proximal actuating mechanism. FIG. 5 shows an overall schematic view of another configuration wherein the aspiration catheter 2 extends through a partial length of the support catheter 1. A vacuum source 8 may be attached to the catheter hub 12 via aspiration source tubing 9. External to or part of the hub 12 are a battery 10 and a cam shaft with motor 11. This motor 11 automatically moves the aspiration catheter 2 out of and back into the valve 4 via a push wire 15.

In these configurations, the vacuum may be applied to the support catheter 1 while the operational times of the system are not limited, the aspiration catheter 2 may be exposed distally to the valve 4 two (2) to 10 times a second. This roughly translates (depending on the system calibration and operating parameters) to exposure time of at least about 0.05 seconds and/or less than or equal to about 0.25 seconds or more, and charged behind the valve 4 for at least about 0.05 seconds and/or less than or equal to about 0.25 seconds or more, although with asymmetric operating parameters charge time may increase to 0.5 seconds or more, so that enough time to clear the aspiration lumen and pressure is built up to allow vacuum force surge in addition to the mechanical force and so that the full potential of that transient power surge. The aspiration catheter 2 may be exposed distally to the valve 4 for less time than the aspiration catheter 2 is behind the valve 4. Aspiration time can be less than or equal to about 1 second, or less than or equal to about 0.5 seconds, less than or equal to about 0.25 seconds, or less than or equal to about 0.1 seconds, or less than or equal to about 0.5 seconds. For example, aspiration time can be between about 0.5 seconds to 0.25 seconds, or between 0.25 seconds and 0.5 seconds, or between 0.5 seconds and 1.0 second. Charge time can be less than or equal to about 1 second, less than or equal to about 0.5 seconds, less than or equal to about 0.25 seconds, or less than or equal to about 0.1 seconds, or less than or equal to about 0.5 seconds. For example, charge time can be between about 0.5 seconds to 0.25 seconds, or between 0.25 seconds and 0.5 seconds, or between 0.5 seconds and 1.0 second. In some methods, aspiration time can be the same as charge time. In other methods, aspiration time can be less than charge time.

The aspiration catheter may also be in threaded contact with the support catheter so that it will advance and pull back when rotated in one direction or the other to provide additional shear forces.

The aspiration catheter lumen may have a circular opening with a diameter to fit the target anatomy. For most applications, the inner diameter of the inner aspiration catheter may be in the range of 0.5 mm to 6 mm for arteries and up to 10 mm or more for veins, with specific embodiments having different diameters specific to their applications. For example, the diameter may be at least about 1 mm and/or less than or equal to about 12 mm, for example at least about 3 mm and/or less than or equal to about 12 mm, such as between about 1 mm to about 3 mm, between about 2 mm to about 4 mm, or between about 3 mm to 6 mm. For example, if calibrated for use in ischemic stroke, the aspiration catheter's internal lumen opening may have a diameter in the range of 0.030" to 0.070" and in extreme cases it can range from 0.020" to 0.090."

The gap between the aspiration catheter and the support catheter may be sealed by design or by a vacuum sealant material such as a sheet of polyurethane or other polymer which can be attached between the proximal ends of the support catheter and the aspiration catheter, preventing the aspiration of air from outside the support catheter (if the interface between the tubes is external to the body lumens) and maintaining good vacuum at the distal tip. The proximal ends of both aspiration and support catheters may also be held within a larger vacuum-sealed container.

Alternatively, as shown in FIG. 9A, fluid may be allowed to enter this space between the inner aspiration catheter 2 and the outer support catheter 1 along flow path 23. FIG. 9A shows a cross section of configuration wherein fluid flow 23 is allowed to enter the gap between the support catheter 1 and the aspiration catheter 2 so that thrombus 5 will be continuously aspirated through the aspiration lumen 3, even when the distal valve 4 is closed. Fluid entering this space will enable a small continuous flow of fluid as shown in FIG. 9B. FIG. 9B shows the same embodiment with the aspiration catheter 2 extended through the valve 4 so that there is no flow from the support catheter 1 to the aspiration catheter 2. In some methods, irrigation flow can be halted when the aspiration catheter 2 is advanced through the valve 4. But in other methods, irrigation flow can be continuous regardless of whether the valve 4 is open or closed.

Where small amount of fluid (blood if within the body or other fluid from a designated reservoir or feedback system otherwise) is allowed to enter in this manner, the pieces of thrombus 5 broken off and sucked into the aspiration catheter 2 will be continuously aspirated through the aspiration lumen 3 and at a higher rate once the aspiration valve 4 is closed, providing self-cleaning and further enhancing the effectiveness of the system by reducing total aspiration time. With this mechanism, the broken off piece of thrombus 5 will not obstruct the tip of the aspiration catheter 2 as it moves back out through the valve 4 and breaks off another piece of thrombus 5, in its active state of operation. The fluid may be provided to the space between the aspiration catheter 2 and the support catheter 1 by a separate fluid supply lumen within the body of the support catheter 1 or through a separate lumen navigated into the body in parallel with the support catheter 1. This fluid may be blood, saline or another solution of water and some solute supplied by an external saline source. FIGS. 9A and 9B show states of operations: (1) aspiration catheter 2 is out of the valve 4 actively aspiration the clots 5 as depicted in FIG. 9B and (2) aspiration catheter 2 is within the support catheter 1, the valve 4 is sealed and self-cleaning is active as depicted in FIG. 9A.

Figure 10:
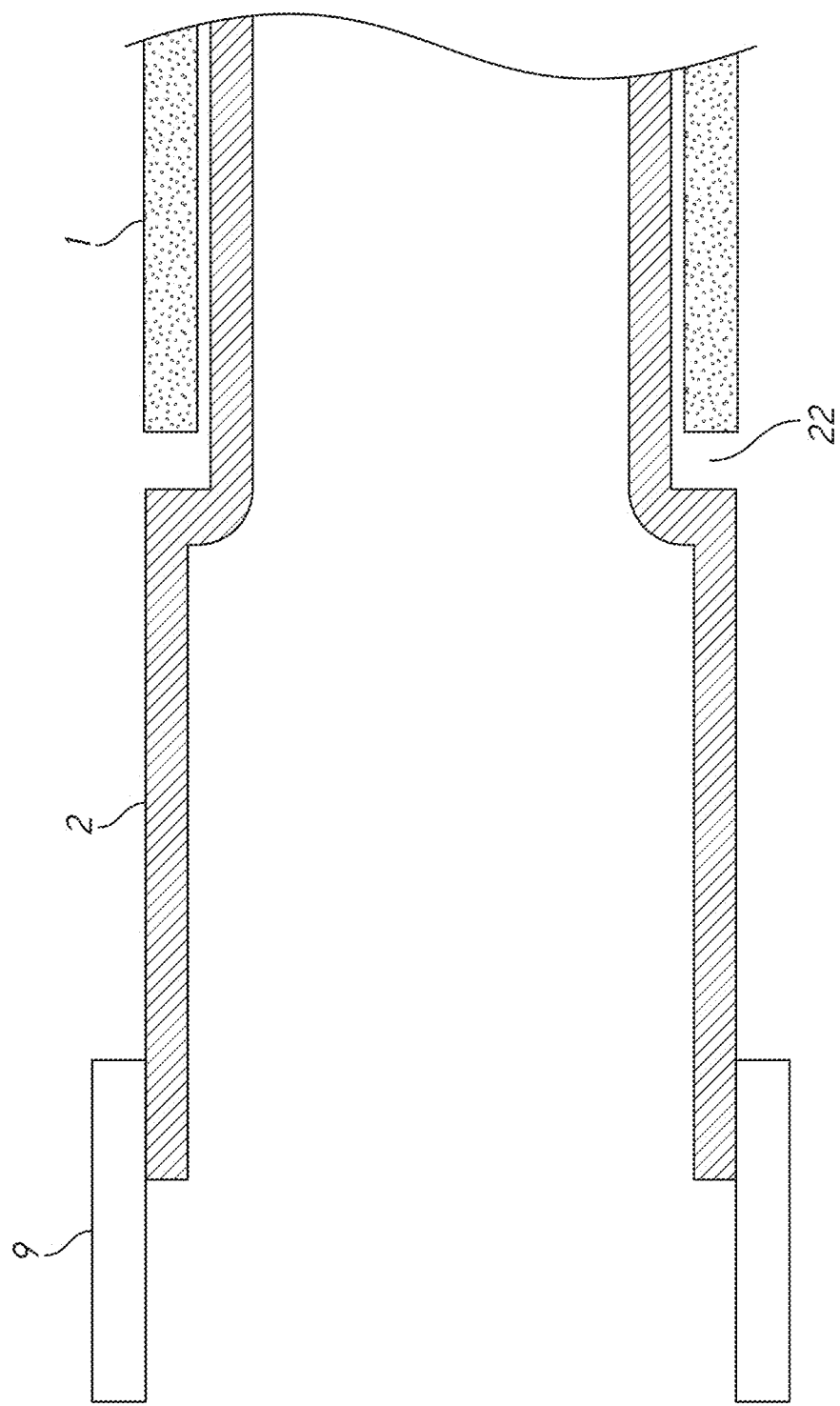
FIG. 10 shows a cross section of another system wherein a stopper joint prevents insertion of the aspiration catheter beyond a safe distance.

In order to prevent vessel trauma or distal pressure on the thrombus, the aspiration catheter 2 cannot protrude out of the valve 4 at high speed beyond a safe distance. Such distance is evaluated for each target anatomy (peripheral, coronary, neurovascular or other) depending on the size and complexity of the surrounding anatomy. To prevent this, a stopper can be used in the proximal side. In one example of a stopper the proximal end of the aspiration catheter 2 may have the same outer diameter as the support catheter 1 up until a point (around reference 22). Distal to that point, the aspiration catheter 2 may have an outer diameter less than the inner diameter of the support catheter 1. This stopper joint 22 allows the aspiration catheter 2 to be inserted into the support catheter 1 up to a certain length and restricting insertion beyond that length. This embodiment is shown in FIG. 10. FIG. 10 shows a cross section of a configuration wherein a stopper joint 22 prevents the insertion of the aspiration catheter 2 beyond a safe distance. Other mechanism for stopping the aspiration catheter 2 from over protruding include mechanical, electrical, and pneumatic solutions. For example, FIGS. 8A and 8B show a separate stopper 22 positioned around the aspiration catheter 2. As another example, a drive unit can be programmed to limit the travel distance of the aspiration catheter 2.

Figure 11:
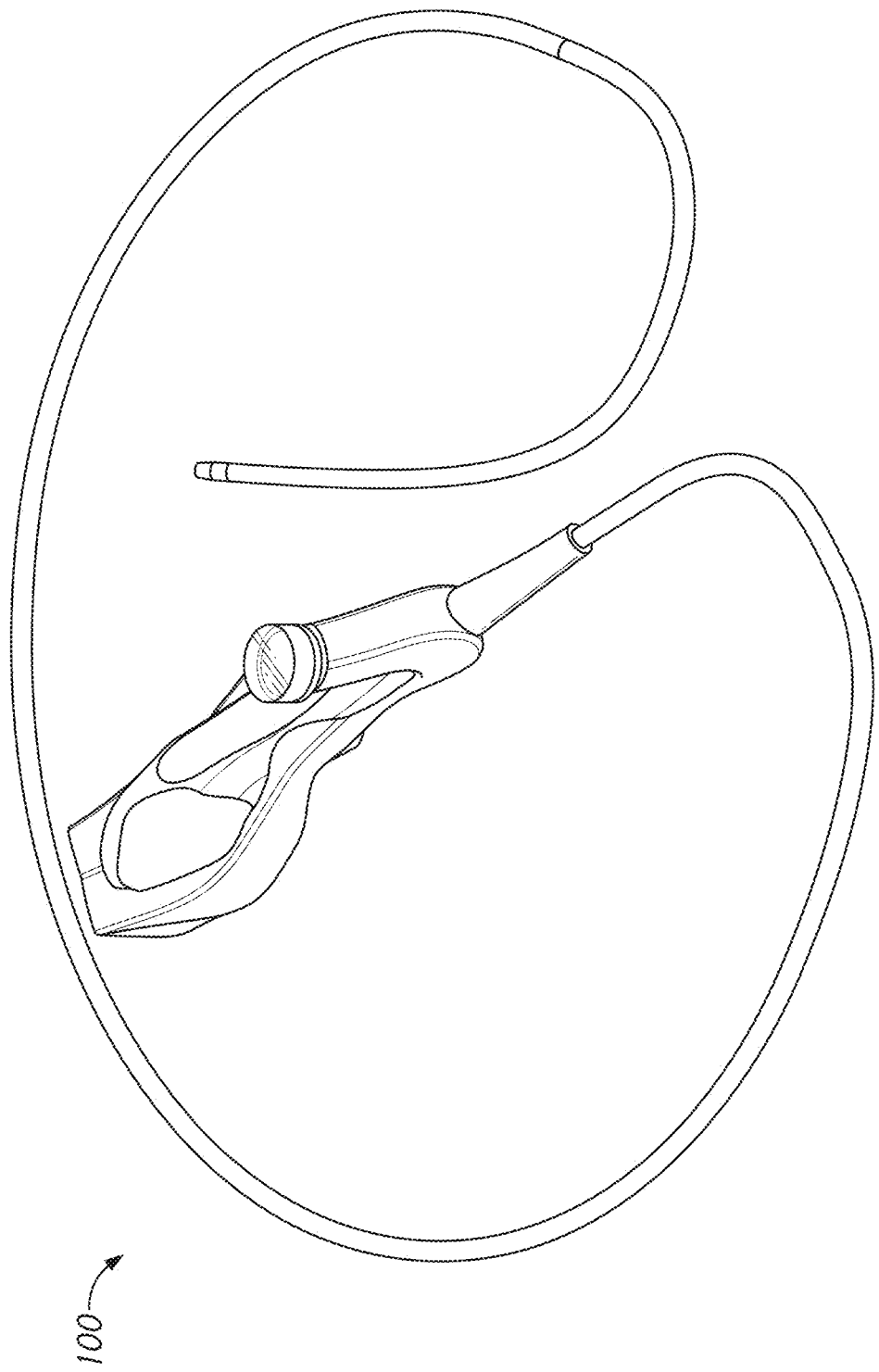
FIG. 11 illustrates an aspiration catheter assembly.

FIG. 11 illustrates a catheter assembly 100 of an aspiration catheter system. The catheter assembly 100 may include any of the features of the catheter systems described above, including an outer support catheter and an inner aspiration catheter.

Figure 12:
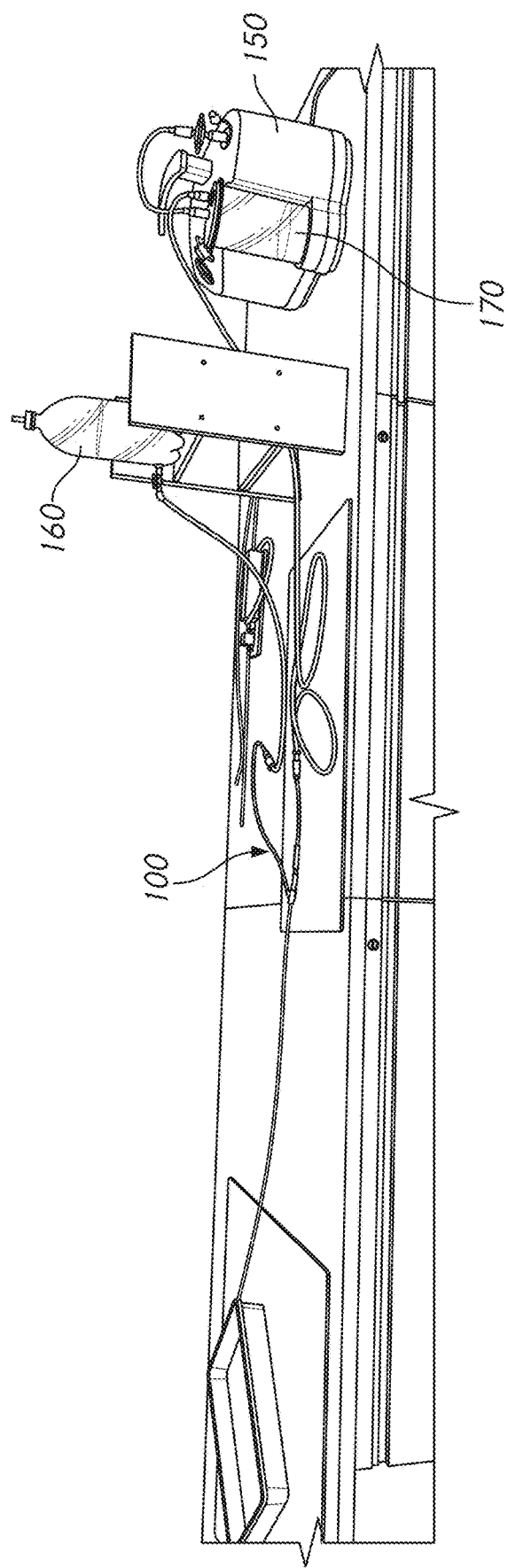
FIG. 12 illustrates an aspiration catheter system with a vacuum source and irrigation source.

FIG. 12 illustrates the aspiration catheter system having the catheter assembly 100 in operable connection to a vacuum source 150 and an irrigation source 160. The aspiration catheter system can include a container 170 to collect clots and fluid aspirated by the catheter assembly 100. In the methods described herein, the vacuum source and/or the irrigation source can supply continuous and constant flow or pressure.

FIGS. 13A to 13E provide schematic representations of the catheter assembly 100 during different stages of the thrombectomy procedure. As illustrated, the catheter assembly 100 can include an outer support catheter 102 and an inner aspiration catheter 104 extending through the support catheter 102.

The aspiration catheter 104 can define an aspiration lumen 106. The aspiration catheter 104 can be operably connected to a vacuum source (see FIG. 12). The vacuum source can cause the aspiration catheter 104 to aspirate clot(s) C through the aspiration lumen 106.

The aspiration catheter 104 can include a polymeric material with a reinforcing braid or coil. An outer diameter of the aspiration catheter 104 can be at least about 1.0 mm and/or less than or equal to about 12.0 mm, for example between 2.0 mm and 10.0 mm, such as no more than 5.0 mm, no more than 4.0 mm, or no more than 3.0 mm. A wall thickness of the aspiration catheter 104 can be less than or equal to about 0.5 mm, less than or equal to about 0.4 mm, less than or equal to about 0.3 mm, less than or equal to about 0.2 mm, or less than or equal to about 0.1 mm.

Figure 13A:
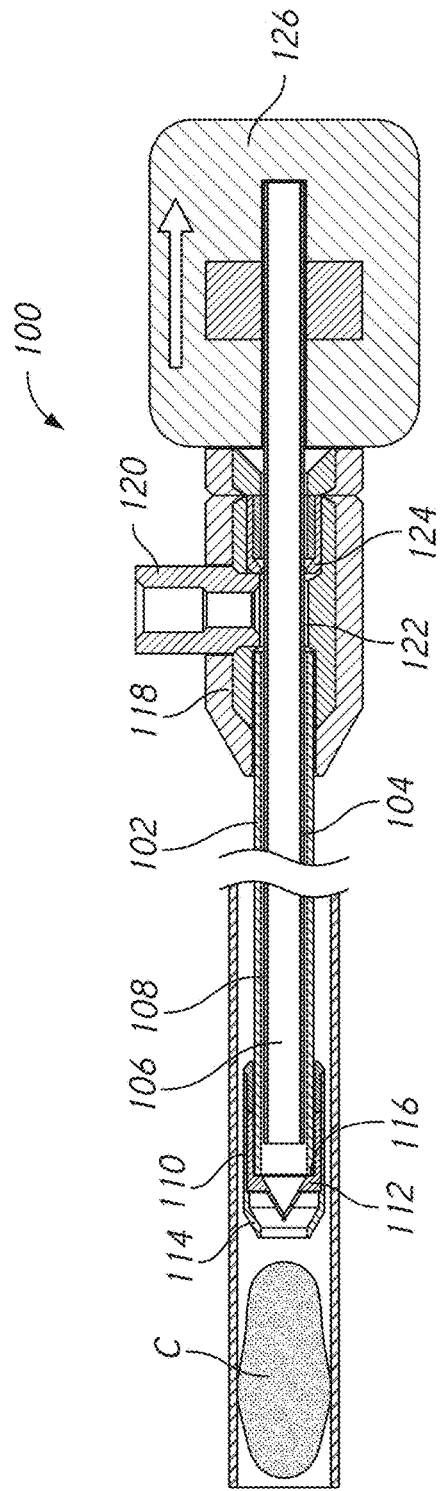
FIGS. 13A to 13E illustrate a method of aspirating a clot using the aspiration catheter assembly.

As shown in FIG. 13A, the aspiration lumen 106 may have a constant diameter. A distal segment of the aspiration catheter 104 may include a first material and a proximal segment of the aspiration catheter may include a second material with different properties, e.g., different stiffness than the first material.

Figure 14:
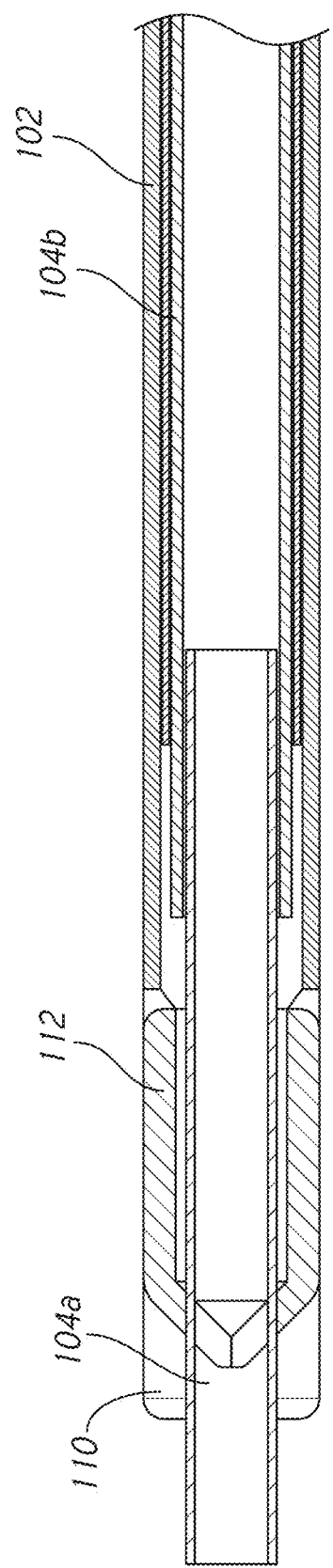
FIG. 14 illustrates a distal segment of the aspiration catheter assembly.

In other embodiments, the aspiration lumen 106 may have a variable diameter with a distal portion of the lumen 106 having a smaller diameter than a proximal portion of the lumen 106. As shown in FIG. 14, the aspiration catheter 104 may include a distal segment 104a joined to a proximal segment 104b. The distal segment 104a and the proximal segment 104b may include the same material or different materials. For example, the proximal segment 104b may be stiffer than the distal segment 104a. The distal segment 104a may have a first inner diameter and the proximal segment 104b may have a second inner diameter greater than the first inner diameter. The distal segment 104a may extend into the proximal segment 104b such that an exterior surface of the distal segment 104a is joined to an inner surface of the proximal segment 104b. An outer diameter of the proximal segment 104b may be less than the inner diameter of the valve housing 110. The transition between the distal segment 104a and the proximal segment 104b may form a stop joint that prevents the aspiration catheter 104 from moving a certain distance beyond a distal end of the support catheter 102. For example, the aspiration catheter may only be able to extend no more than 5 cm (or no more than 3 cm, or no more than 2 cm, no more than 1 cm, no more than 0.5 cm, or no more than 0.1 cm) beyond a distal end of the support catheter 102. It is possible however to manually or slowly extend the aspiration tube out of the support tube for a longer distance in a "seeker" mode to complete the procedure if there is a remaining clot in a small distal vessel, to capture this residual clot and rapidly retract it back into the support tube.

The support catheter 102 can include an elongate tubular body. The elongate tubular body can include a polymeric material with a reinforcing braid or coil. One or more radiopaque markers may be located along the elongate tubular body.

An inner diameter of the support catheter 102 can be greater than an external diameter of the aspiration catheter 104 to leave space 108 for fluid to flow between the two catheters. An outer diameter of the support catheter 102 can be at least about 1.0 mm and/or less than or equal to about 12.0 mm, for example between 2.0 mm and 10.0 mm or between 3.0 mm and 5.0 mm. An inner diameter of the support catheter 102 can be at least 0.1 mm greater than an outer diameter of the aspiration catheter 104, for example at least about 0.1 mm greater than the outer diameter of the aspiration catheter 104 and/or no more than about 1.0 mm greater the outer diameter of the aspiration catheter 104, for example between about 0.25 mm and about 0.75 mm greater than the outer diameter of the aspiration catheter 104. A wall thickness of the support catheter 102 can be less than or equal to about 0.5 mm, less than or equal to about 0.4 mm, less than or equal to about 0.3 mm, less than or equal to about 0.2 mm, or less than or equal to about 0.1 mm.

The support catheter 102 can include a valve 112 at or near a distal end 116 of the elongate tubular body. For example, the valve 112 can be within 15 cm (or within 10 cm, or within 5 cm, within 1 cm, within 0.5 cm, or within 0.1 cm) of the distal end 116 of the elongate tubular body. The valve 112 may be disposed within a lumen of the support catheter 102 or external of the support catheter 102. The valve 112 can be secured to the elongate tubular body using any of the features described above with respect to the valve 4.

As illustrated, the valve 112 can be secured to the elongate tubular body with a valve housing 110. The valve housing 110 can protect the vessel wall from the valve 112. The valve 112 may be disposed within the valve housing 110 with the valve housing 110 extending distally and/or proximally of the valve 112. The valve 112 may be mechanically or chemically secured within the valve housing 110.

The valve housing 110 can be secured to a distal end 116 of the elongate tubular body, for example by welding or bonding. The valve housing 110 may be secured to an exterior surface of the elongate tubular body. The valve housing 110 can be made of plastic or metal.

An inner diameter of the valve housing 110 may be larger than an inner diameter of the elongate tubular body. But in other arrangements, the valve housing 110 may extend into the elongate tubular body. A diameter of the opening at the distal tip 114 may be less than or equal to the inner diameter of the distal end 116 of the elongate tubular body. The distal tip 114 of the valve housing 110 may form the distal tip of the support catheter 102. The distal tip 114 of the valve housing 110 may be tapered. The tapered distal tip 114 can function as a breaking shoulder to disrupt or segment the clot. This helps segment harder clots.

When assembled, the distal end 116 of the elongate tubular body may abut a proximal side of the valve 112 to maintain a position of the valve 112 within the valve housing 110. The distal end 116 of the elongate tubular body may be spaced apart from a proximal facing surface of the valve 112 to allow irrigation fluid to flow into the aspiration catheter 104.

The valve housing 110 is optional. The valve 112 may be incorporated directly onto or into the elongate tubular body. For example, a metal ring may be placed within the valve 112 and welded to the reinforcement structure within the elongate tubular body.

The valve 112 can be a one-way valve. As illustrated, the valve 112 is a duckbill valve but may include any of the valve features described above. The valve 112 could be any valve with an opening edge sufficiently rigid to segment a clot. The valve 112 could be any valve that allows the aspiration catheter 104 to be advanced and retracted through the valve 112. For example, the valve 112 could be a slit valve or a valve with overlapping leaflets having edges suitable for segmenting the valve. An inner diameter of the valve 112 can be less than an inner diameter of the support catheter 102 but greater than an outer diameter of the aspiration catheter 104.

The catheter assembly 100 may include a manifold 118 at the proximal end of the support catheter 102. The manifold 118 may include an inlet 120 for connection to an irrigation source (see FIG. 12). The manifold 118 allows irrigation fluid to flow in the space 108 between the support catheter 102 and the aspiration catheter 104. The manifold 118 also includes a passage 122 through which the aspiration catheter 104 extends for connection to a vacuum source.

The passage 122 may include a seal member 124 for preventing fluid irrigation fluid from flowing out of the space outside of the aspiration catheter 104. The seal member 124 can provide less than 360 degrees of contact with the aspiration catheter 104. For example, the seal member 124 can have one or more lobes or prongs for interfacing with the aspiration catheter 104, for example two lobes or three lobes or four lobes. The separate contact points decrease the amount of friction between the aspiration catheter 104 and the seal member 124 and enable the use of a lower torque motor.

The inner aspiration catheter 104 is capable of being manually or automatically moved within the lumen of the support catheter. When automated, the catheter assembly 100 may include a drive unit 126. The drive unit 126 may include a motor for driving the aspiration catheter 104 relative to the support catheter 102. The drive unit 126 may include or be operably connected to a controller configured to cause the motor to advance and retract the aspiration catheter. The drive unit 126 may include a battery source. The drive unit 126 may be a handheld component that is separately attachable to the aspiration catheter 104. For example, the same drive unit 126 may be used with disposable catheter assemblies.

FIG. 13A illustrates the catheter assembly 100 in a closed position with the aspiration catheter 104 retracted relative to the valve 112. In this configuration, irrigation fluid (e.g., saline) flows through the catheter assembly 100 to lubricate the system and vacuum builds up at the distal end of the catheter assembly 100.

As the aspiration catheter 104 is advanced (see FIG. 13B), the valve 112 opens outward. The valve 112 can be made of a material that forms a seal against the aspiration catheter 104 and prevents irrigation fluid from flowing out of the support catheter 102. When the valve 112 opens, the vacuum build up increases engagement between the clot C and the aspiration catheter 104.

The action of moving the blood clot towards the catheter opening is done by inducing a flow field that create forces on the blood clot, in the direction of the catheter opening. But there is a fundamental physical limit to the maximum vacuum level that can be built in the vasculature, which is 1 bar. Conventional aspiration devices rely on high blood flow to move the blood clot toward the catheter, but there is insufficient blood flow in different areas of the vasculature for adequate aspiration. Unlike conventional systems, the catheter assembly 100 minimizes dependency on flow rate.

Figures 15A, 15B:
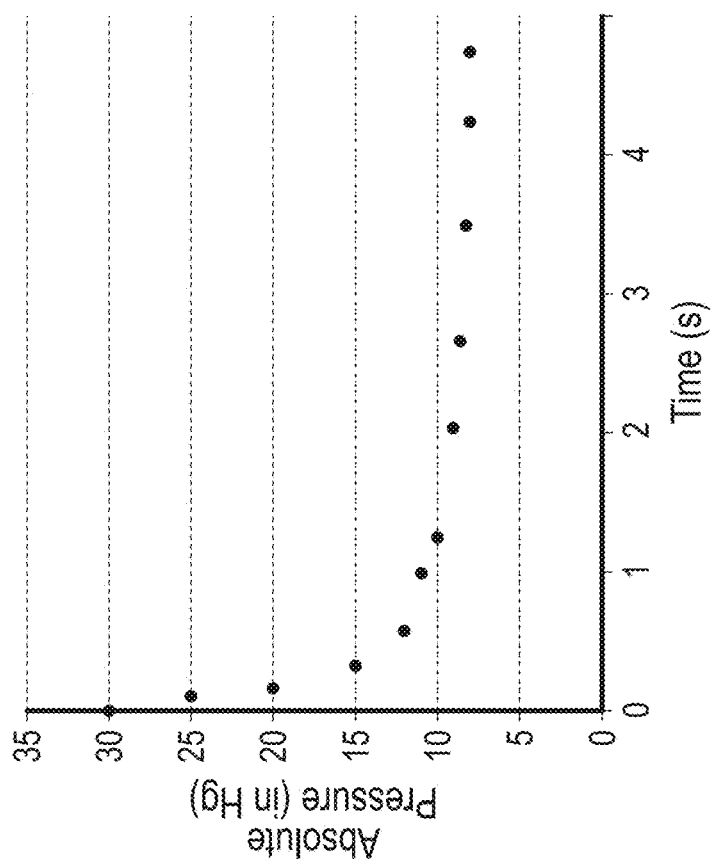
FIGS. 15A and 15B show representative traces of the vacuum pressure charging and discharging at the distal tip of the catheter assembly when flow is stopped and restarted using the aspiration catheter assembly.

The catheter assembly 100 builds up pressure at the distal end of the catheter assembly 100 such that absolute pressure is at least about 25 inHg and/or less than or equal to about 35 inHg, such as at least about 26 inHg and/or less than or equal to about 33 inHg when the valve 112 opens (see FIG. 15B). The absolute pressure at the distal end of the catheter assembly 100 may be at least about 15 inHg, at least about 20 inHg, at least about 25 inHg, at least about 30 inHg, or at least about 35 inHg when the valve 112 opens. This creates a sufficient flow field to move the clot C toward the aspiration catheter 104. Moreover, clot acquisition is made easier by moving the aspiration catheter 104 distally and closer to the clot C.

As the aspiration catheter 104 is retracted, the aspiration catheter 104 has sufficient engagement with the clot C to pull the clot C into the support catheter 102. The extrusion force may be increased by adding a water pressure column as discussed below with respect to FIG. 13E. When the aspiration catheter 104 is retracted proximal of the valve 112, the valve 112 closes. As shown in FIGS. 13C and 13D, the valve housing 110 disrupts the clot C and the valve 112 breaks the clot C into pieces. The valve 112 alone or in combination with valve housing 110 can improve segmentation.

In conventional systems, increased clot length within the catheter and wall friction provide resistance to aspiration. This causes clogs. To decrease the clot length, the catheter assembly 100 breaks the clot against the distal tip 114 of the valve housing 110 and/or the valve 112. The combination of vacuum force on one side of the clot C and shear forces of the catheter assembly 100 on the clot C cause segmentation. This step leverages clot weakness to shear forces to decrease clot length and minimize friction.

The steps shown in FIGS. 13A to 13D are repeated until the entire clot C has been aspirated. The steps may be repeated at least 2× per second, at least 3× per second, at least 4× per second, at least 5× per second, at least 6× per second, at least 7× per second, at least 8× per second, at least 9× per second, or at least 10× per second.

During this process, a positive pressure may be applied within the aspiration lumen 106. For example, there may be a periodic or continuous flow of irrigation fluid as illustrated in FIG. 13E. This helps push the macerated clot pieces through the aspiration catheter 104 and exit to the container 170. Moreover, the irrigation flow prevents air bubbles from forming within the catheter assembly 100.

As shown in FIG. 13E. fluid flows between the outer surface of the aspiration catheter 104 and the inner surface of the support catheter 102. When the irrigation fluid reaches the valve 112, the irrigation fluid enters the distal end of the aspiration catheter 104 and pushes the macerated clot segments proximally through the aspiration catheter 104 as vacuum force aspires the clot segments. Adding water pressure can double the force of the vacuum to at least about 1 bar and/or less than or equal to about 2 bar. The added propellant speeds up aspiration and prevents clogging. The positive pressure may be applied using other methodologies, for example using a pump.

If the aspiration catheter 104 is clogged, the aspiration catheter 104 can be retracted proximal of the valve 112 without pulling the aspiration catheter 104 completely out of the body. This increases the suction of irrigation fluid. The irrigation flow will unclog the aspiration catheter 104. In some methods, irrigation flow may only be activated when non-continuous flow (clog) is detected or irrigation flow may be increased when non-continuous flow is detected.

During this process, the aspiration catheter 104 may remain stationary or be advanced and retracted while still remaining behind the distal valve 112.

Figure 13B:
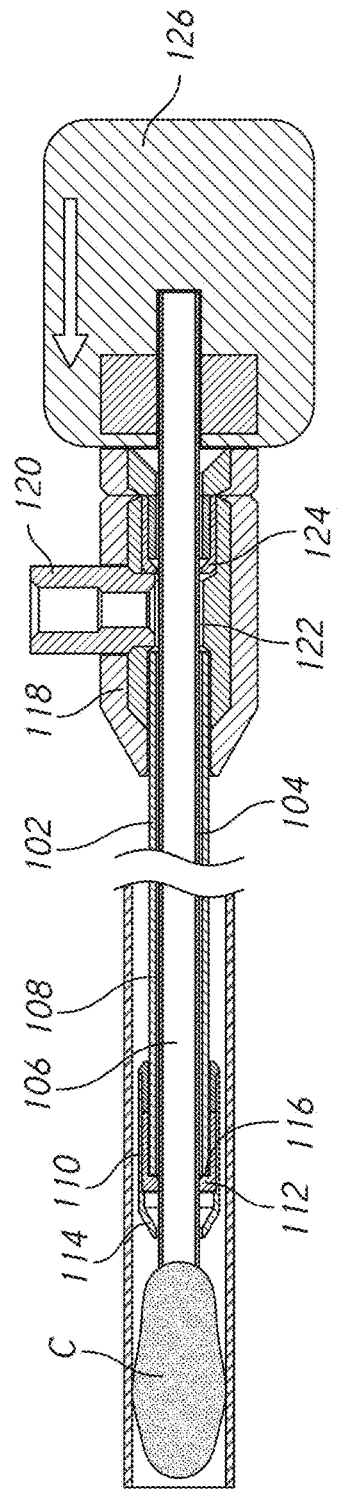
Figure 13C:
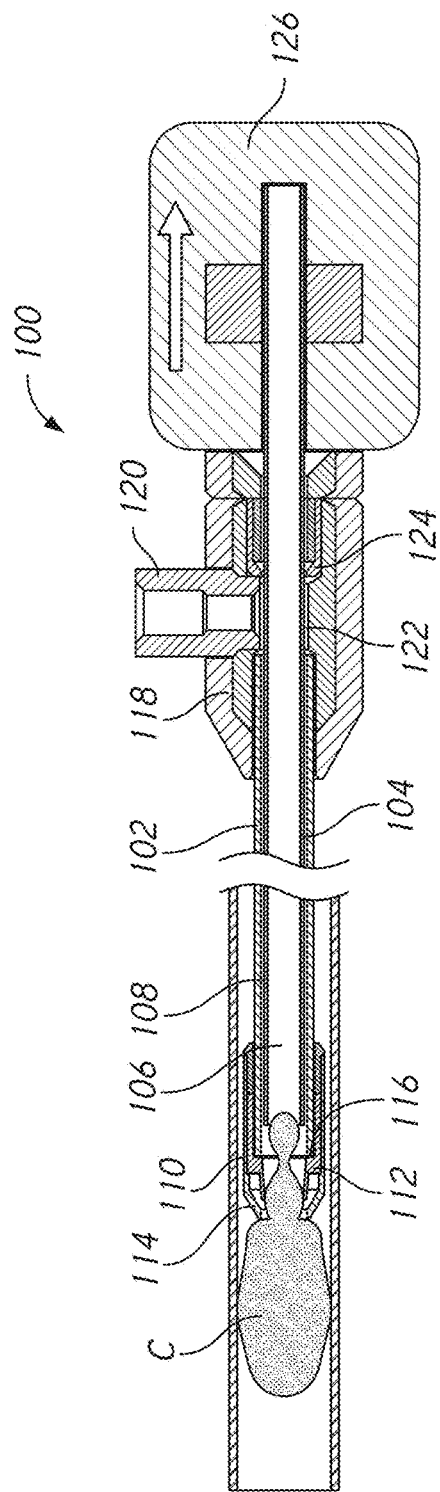
Figure 13D:
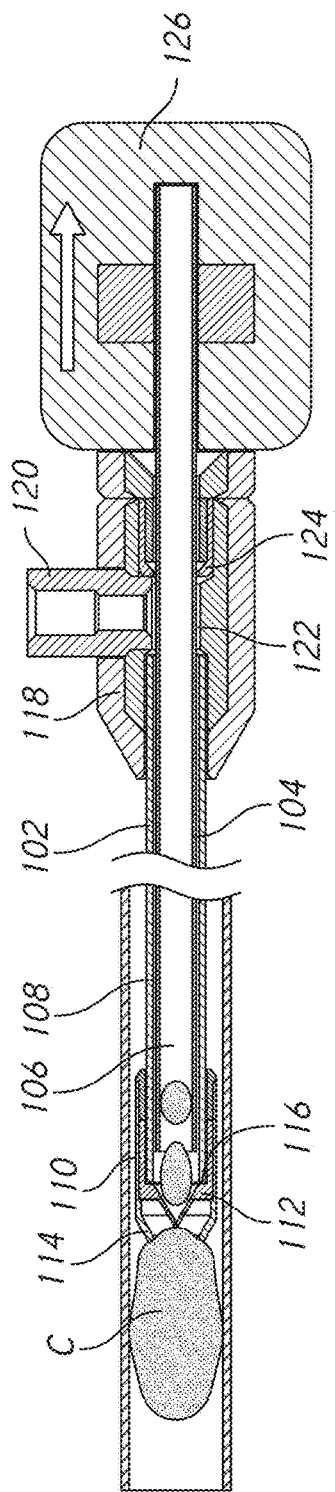
Figure 13E:
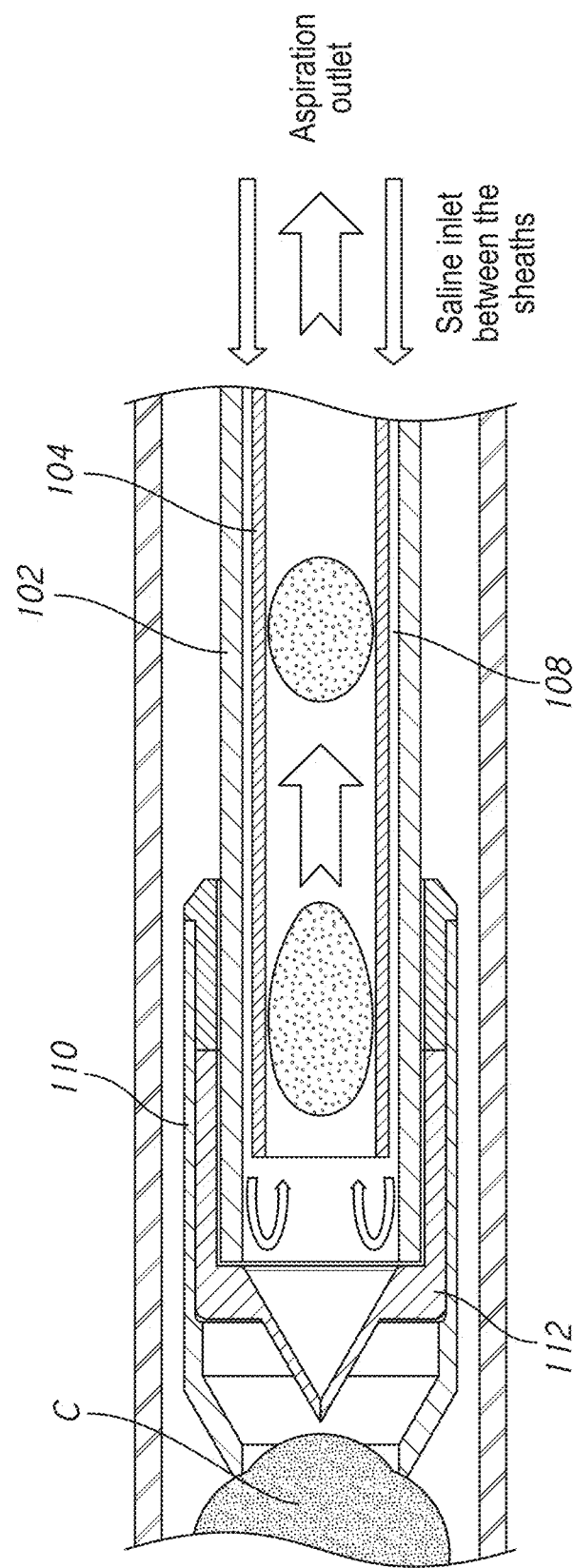

FIGS. 15A and 15B show representative traces of the vacuum pressure charging and discharging at the distal tip of the aspiration catheter 104 when flow is stopped (FIG. 13A) and restarted (FIG. 13B).

Terminology

Although certain aspiration catheter systems and methods have been described herein with a dual catheter system having a support catheter and inner aspiration catheter, the principles of the systems and methods described herein can executed with a single catheter system having a different type of valve, for example an automated valve. Moreover, although the support catheter and inner aspiration catheter provide concentric irrigation and aspiration lumens, other configurations are possible, for example separate and non-concentric lumens.

As used herein, the relative terms "proximal" and "distal" shall be defined from the perspective of the catheter system. Thus, proximal refers to the direction of the handle and distal refers to the direction of the aspiration tip.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Although certain embodiments and examples have been described herein, it will be understood by those skilled in the art that many aspects of the delivery systems shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

Conditional language used herein, such as, among others, "can," "might," "may," "e.g.," and the like, unless specifically stated otherwise, or otherwise understood within the context as used, is generally intended to convey that some embodiments include, while other embodiments do not include, certain features, elements, and/or states. Thus, such conditional language is not generally intended to imply that features, elements, blocks, and/or states are in any way required for one or more embodiments or that one or more embodiments necessarily include logic for deciding, with or without author input or prompting, whether these features, elements and/or states are included or are to be performed in any particular embodiment.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±1%, ±5%, ±10%, ±15%, etc.). For example, "about 1.0 mm" includes "1.0 mm."

What is claimed is:

1. An aspiration catheter assembly for removing a clot, the aspiration catheter assembly comprising:
   a support catheter comprising an elongate tubular body and a valve for controlling a level of vacuum at a distal end of the support catheter;
   an aspiration catheter disposed within the support catheter, a distal end of the aspiration catheter configured to repeatedly translate distally and proximally of the distal end of the support catheter, the aspiration catheter comprising an aspiration lumen for receiving at least a portion of the clot; and
   a stopper configured to prevent the distal end of the aspiration catheter from moving beyond a preset distance from the distal end of the support catheter.

2. The aspiration catheter assembly of claim 1, wherein the valve prevents irrigation flow out of the support catheter.

3. The aspiration catheter assembly of claim 1, wherein the valve opens when the aspiration catheter is advanced through the valve, and wherein the valve closes when the aspiration catheter is retracted proximal of the valve.

4. The aspiration catheter assembly of claim 1, wherein the support catheter comprises a valve housing secured to a distal end of the elongate tubular body, the valve housing comprising the valve.

5. The aspiration catheter assembly of claim 1, further comprising:
   a motor operably connected to the aspiration catheter; and
   a controller configured to cause the motor to advance and retract the aspiration catheter relative to the valve of the support catheter.

6. The aspiration catheter assembly of claim 1, further comprising a space between the aspiration catheter and the support catheter for irrigation fluid.

7. The aspiration catheter of claim 1, wherein the stopper is configured to prevent the aspiration catheter from moving more than a preset distance of up to 5 centimeters beyond a distal end of the support catheter.

8. An aspiration catheter assembly for removing a clot, the aspiration catheter assembly comprising:
   a support catheter configured to be in fluid connection with an irrigation source;
   an aspiration catheter configured to be in fluid connection with a vacuum source, the aspiration catheter disposed within the support catheter and capable of moving relative to the support catheter, the aspiration catheter comprising an aspiration lumen for receiving at least a portion of the clot; and
   a valve for controlling a level of vacuum at a distal end of the aspiration catheter assembly and preventing irrigation flow out of the distal end of the aspiration catheter assembly;
   wherein the aspiration catheter is configured to move between an extended position when a distal end of the aspiration catheter is advanced distal of the valve and a retracted position when the distal end of the aspiration catheter is retracted proximal of the valve;
   wherein in the retracted position, fluid from the irrigation source is allowed to flow through a space between the support catheter and the aspiration catheter, into the distal end of the aspiration catheter, and proximally out of the aspiration catheter; and
   wherein in both the retracted position and in the extended position, fluid from the irrigation source does not flow out of the distal end of the support catheter.

9. The aspiration catheter assembly of claim 8, wherein the valve is at a distal end of the support catheter.

10. The aspiration catheter assembly of claim 8, wherein the support catheter comprises a valve housing at a distal end of the support catheter, the valve housing comprising the valve.

11. The aspiration catheter assembly of claim 8, further comprising:
    a motor operably connected to the aspiration catheter; and
    a controller configured to cause the motor to advance and retract the aspiration catheter relative to the valve.

12. The aspiration catheter assembly of claim 8, further comprising a space between the aspiration catheter and the support catheter for irrigation flow.

13. The aspiration catheter of claim 8, further comprising a manifold at a proximal end of the support catheter, the manifold comprising an inlet for fluid connection with an irrigation source and a passage through which the aspiration catheter extends for fluid connection with a vacuum source.

14. The aspiration catheter of claim 13, further comprising a seal member disposed within the passage to prevent irrigation flow from flowing out of a space within the passage and outside of the aspiration catheter.

* * * * *

UNITED STATES PATENT AND TRADEMARK OFFICE
CERTIFICATE OF CORRECTION

| | | |
|---|---|---|
| PATENT NO. | : 12,369,933 B2 | Page 1 of 1 |
| APPLICATION NO. | : 18/590717 | |
| DATED | : July 29, 2025 | |
| INVENTOR(S) | : Eitan Konstantino | |

It is certified that error appears in the above-identified patent and that said Letters Patent is hereby corrected as shown below:

In the Claims

In Column 22, Claim 7, Line 4, delete "aspiration catheter of" and insert --aspiration catheter assembly of--.

In Column 22, Claim 13, Line 48, delete "aspiration catheter of" and insert --aspiration catheter assembly of--.

In Column 22, Claim 14, Line 53, delete "aspiration catheter of" and insert --aspiration catheter assembly of--.

Signed and Sealed this
Fourth Day of November, 2025

John A. Squires
*Director of the United States Patent and Trademark Office*